United States Patent
Sagar et al.

(10) Patent No.: US 9,023,763 B2
(45) Date of Patent: May 5, 2015

(54) MODIFICATION OF TREHALOSE-6-PHOSPHATE LEVELS IN PLANTS

(75) Inventors: Ram Sagar, Oxford (GB); Lucia F. Primavesi, Harpenden (GB); Matthew J. Paul, Harpenden (GB); Benjamin G. Davis, Oxford (GB)

(73) Assignee: Isis Innovation Limited, Oxford (GB)

( * ) Notice: Subject to any disclaimer, the term of this patent is extended or adjusted under 35 U.S.C. 154(b) by 43 days.

(21) Appl. No.: 14/113,571

(22) PCT Filed: Apr. 23, 2012

(86) PCT No.: PCT/GB2012/050891
§ 371 (c)(1),
(2), (4) Date: Jan. 9, 2014

(87) PCT Pub. No.: WO2012/146914
PCT Pub. Date: Nov. 1, 2012

(65) Prior Publication Data
US 2014/0113820 A1    Apr. 24, 2014

(30) Foreign Application Priority Data

Apr. 26, 2011 (GB) .................................. 1107031.5
Aug. 5, 2011 (GB) .................................. 1113642.1

(51) Int. Cl.
*A01N 57/24* (2006.01)
*A01N 57/16* (2006.01)
(Continued)

(52) U.S. Cl.
CPC ................ *A01N 57/16* (2013.01); *A01N 57/24* (2013.01); *C07H 11/04* (2013.01); *C07H 15/04* (2013.01)

(58) Field of Classification Search
CPC ....... A01N 57/16; A01N 57/24; C07H 11/04; C07H 15/04
USPC .......... 504/196, 210, 292; 514/25, 53, 75, 99; 549/218, 222
See application file for complete search history.

(56) References Cited

FOREIGN PATENT DOCUMENTS

| CN | 101374952 A | 2/2009 |
|---|---|---|
| JP | H10-218694 A | 8/1998 |

(Continued)

OTHER PUBLICATIONS

Backus et al., "Uptake of unnatural trehalose analogs as a reporter for *Mycobacterium tuberculosis*", 2011; Nature Chemical Biology, 7(4):228-235.*

(Continued)

*Primary Examiner* — Jane C Oswecki
(74) *Attorney, Agent, or Firm* — Kilpatrick Townsend & Stockton LLP

(57) ABSTRACT

Compounds which are trehalose-6-phosphate or trehalose-6-phosphonate precursors of formula (I) or agriculturally acceptable salts thereof are provided: (I) The compounds are useful in increasing starch production in plants.

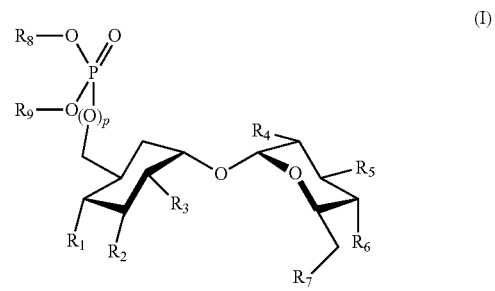

16 Claims, 5 Drawing Sheets

(51) Int. Cl.
   *C07H 11/04* (2006.01)
   *C07H 15/04* (2006.01)

(56) References Cited

FOREIGN PATENT DOCUMENTS

| JP | 2007308434 A | 11/2007 |
|----|--------------|---------|
| WO | 97/42326 A2 | 11/1997 |
| WO | 97/42326 A3 | 11/1997 |
| WO | 2007/085483 A | 8/2007 |
| WO | 2011/030160 A1 | 3/2011 |

OTHER PUBLICATIONS

Mayer et al., Biologically Active Molecules with a "Light Switch", 2006; Angew. Chem. Int. Ed., 45:4900-4921.*
Ellis-Davies, "Caged compounds: photorelease technology for control of cellular chemistry and physiology", 2007, Nature Methods, 4(8):619-628.*
Arslan, Tuncer et al., "Structurally Modified Firefly Luciferase. Effects of Amino Acid Substitution at Position 286," *J. Am. Chem Soc.* (Nov. 12, 1997) 119(45):10878-10887.
Aujard, Isabelle et al., "*o*-Nitrobenzyl Photolabile Protecting Groups with Red-Shifted Absorption: Syntheses and Uncaging Cross-Sections for One- and Two-Photon Excitation," *Chem. Eur. J.* (2006) 12:6865-6879.
Backus, Keriann M. et al., "Uptake of unnatural trehalose analogs as a reporter for *Mycobacterium tuberculosis*," *Nature Chemical Biology* (Apr. 2011) 7(4):228-235.
Backus, Keriann M. et al., "Uptake of unnatural trehalose analogs as a reporter for *Mycobacterium tuberculosis*," *Nature Chemical Biology* (Apr. 2011) 7(4):228-235; *Chem. Abstr.* (2011), No. 155-33727.
Backus, Keriann M. et al., PCT Int. Appl., p. 129, WO 2011/030160 A1 (2011); *Chem Abstr.* (2011), No. 154:355353.
Chary, S. Narasimha et al., "Trehalose-6-Phosphate Synthase/Phosphatase Regulates Cell Shape and Plant Architecture in *Arabidopsis*," *Plant Physiology* (Jan. 2008) 146:97-107.
Delatte, Thierry L. et aL., "Determinaton of trehalose-6-phosphate in *Arabidopsis* seedlings by successive extractions followed by anion exchange chromatography-mass spectrometry," *Analytical Biochemistry* (2009) 389:12-17.
Ellis-Davies, Graham C R, "Caged compounds: photorelease technology for control of cellular chemistry and physiology," *Nature Methods* (Aug. 2007) 4(8):619-628.
Search Report corresponding to Application No. GB1107031.5 dated Jul. 27, 2011, 4 pages.
International Search Report corresponding to Application No. PCT/GB2012/050891 mailed Jul. 2, 2012, 3 pages.
Kalek, Marcin et al., "Microwave-Assisted Palladium-Catalyzed Cross-Couple of Aryl and Vinyl Halides with H-Phosphonate Diesters," *Org. Lett.* (2008) 10(20):4637-4640.
Kolbe, Anna et al., "Trehaolse 6-phosphate regulates starch synthesis via posttranslational redox activation of ADP-glucose pyrophosphorylase," *PNAS* ((Aug. 2, 2005) 102(31):11118-11123.
Laven, Gaston et al., "Palladium(0)-Catalyzed Benzylation of H-Phosphonate Diesters: An Efficient Entry to Benzylphosphonates," *Synlett* (2009) 2:225-228.
Mayer, Gunter et al., Biologically Active Molecules with a "Light Switch," *Angew. Chem. Int. Ed.* (2006) 45:4900-4921.
Meldal, Morten et al., "Large-scale synthesis of D-mannose 6-phosphate and other hexose 6-phosphates," *Carbohydrate Research* (1992) 235:115-127.
Patel, Mitul K. et al., "Flow chemistry kinetic studies reveal reaction conditions for ready access to unsymmetrical trehaolse analogues," *Org. Biomol. Chem.* (2010) 8:4232-4235.
Patel, Mitul K. et al., "Flow chemistry kinetic studies reveal reaction conditions for ready access to unsymmetrical trehaolse analogues," *Org. Biomol. Chem.* (2010) 8:4232-4235; *Chem. Abstr.* (2010), No. 153:580564.
Paul, Matthew, "Trehalose 6-phosphate," *Current Opinion in Plant Biology* (2007) 10:303-309.
Paul, Matthew J., "Trehalose Metabolsim and Signaling," *Annu. Rev. Plant Biol.* (2008) 59:417-441.
Paul, Matthew J., "Upregulation of biosynthetic processes associated with growth by trehaolse 6-phosphate," *Plant Signaling & Behavior* (Apr. 2010) 5(4):386-392.
Pellny, Till K., "Genetic modification of photosynthesis with *E. coli* genes for trehalose synthesis," *Plant Biotechnology Journal* (2004) 2:71-82.
Ronnow, Tor E.C.L. et al., "Gram-scale synthesis of $\alpha,\alpha$-trehalose 6-monophosphate and $\alpha,\alpha$-trehalose 6,6'-diphosphate," *Carbohydrate Research* (1994) 260:323-328.
Scheigetz, John et al., "Synthesis of Fluorescein Phosphorotriesters Using Photolabile Protecting Groups," *Synthetic Communications* (2000) 30(8):1437-1445.
Schluepmann, Henriette et al., "Trehalose 6-phosphate is indispensable for carbohydrate utilization and growth in *Arabidopsis thaliana*," *PNAS* (May 27, 2003) 100(11):6849-6854.
Singh Anil K. et al., "3-Nitro-2-naphthalenemethanol: a photocleavable protecting group for carboxylic acids," *Tetrahedron* (2005) 61:10007-10012.
Smith, Alison M. et al., "Quantification of starch in plant tissues," *Nature Protocols* (2006) 1(3):1342-1345.
Yang, Min et al., "High-Throughput Mass-Spectrometry Monitoring for Multrisubstrate Enzymes: Determining the Kinetic Parameters and Catalytic Activities of Glycosyltransferases," *ChemBioChem* (2005) 6:346-357.
Watanabe, Soichiro et al., "Reductive Ring Opening of *o*-Nitrobenzylidene Acetals of Monosaccharides: Synthesis and Photolysis of Some Photolabile Sugars," *Org. Lett.* (2001) 3(2):255-257.
Yu, Haitao et al., "Chemistry and biological applications of photolabile organic molecules," *Chem. Soc. Rev.* (2010) 39:464-473.
Zhang, Yuhua et al., "Inhibition of SNF1-Related Protein Kinase1 Activity and Regulation of Metabolic Pathways by Trehalose-6-Phosphate," *Plant Physiology* (Apr. 2009) 149:1860-1871.
Eastmond et al., "Is trehalose-6-phosphate a regulator of sugar metabolism in plants?" Journal of Experimental Botany, Jan. 2003, vol. 54(382), pp. 533-537.

* cited by examiner

SnRK1 assay with Examples 1-4 and T6P

Deprotection P NMR of Example 1

SnRK1 activity in presence of 0.32 nM deprotected T6P or Sigma T6P (SEM n=6 for No T6P, n=3 for + T6P)

Good calibration curve for T6P using 2DG6P as internal standard

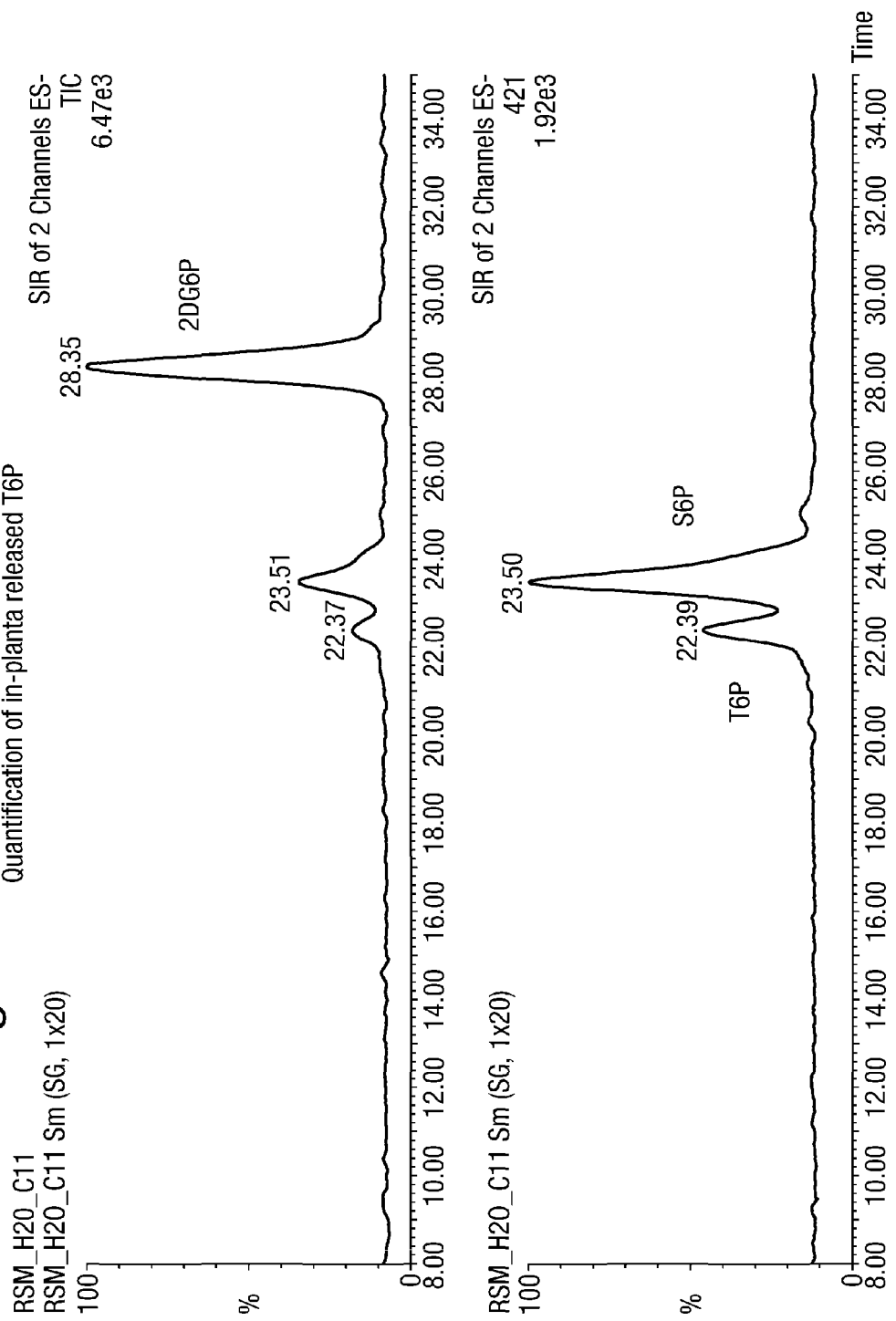

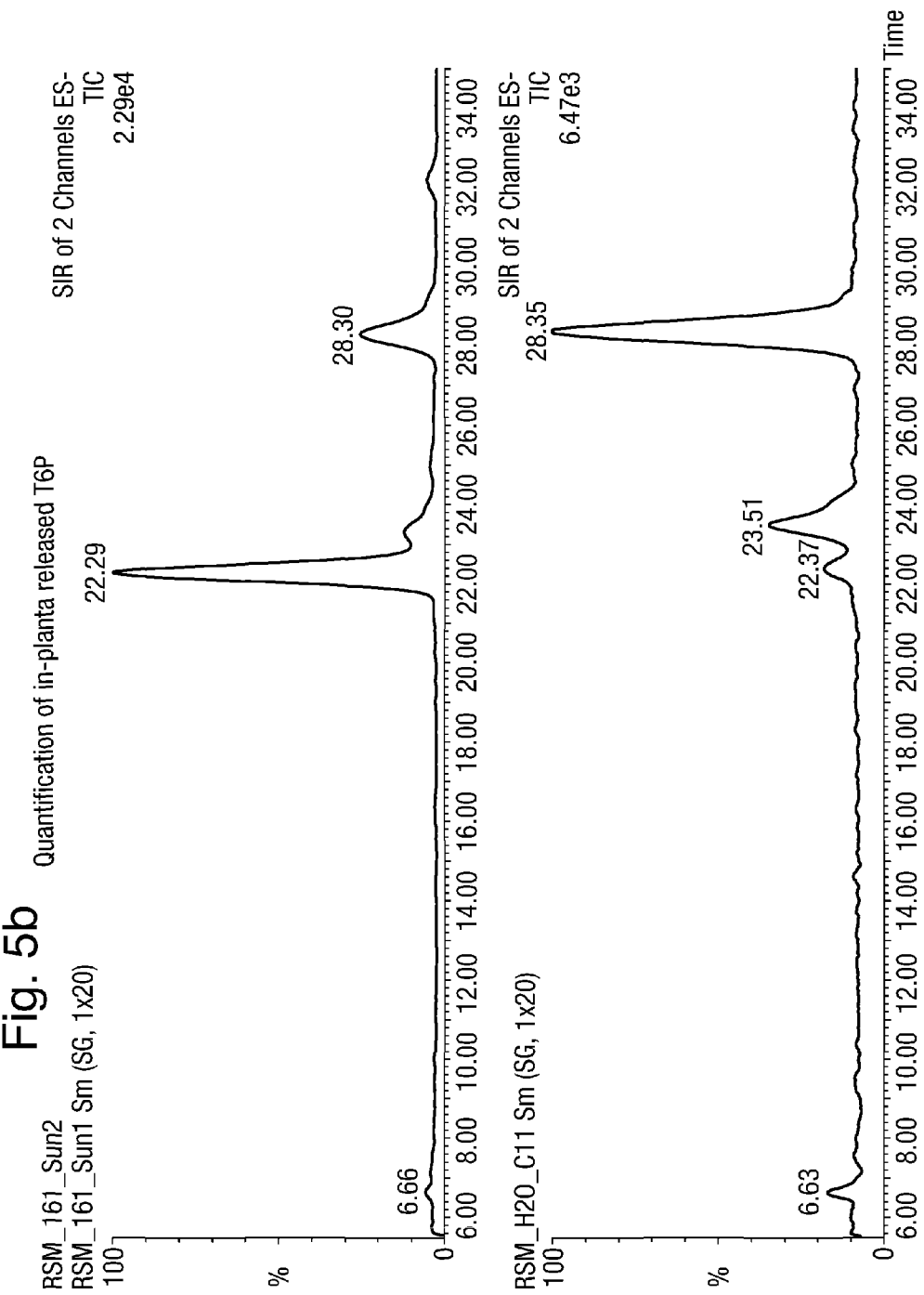

MODIFICATION OF TREHALOSE-6-PHOSPHATE LEVELS IN PLANTS

The invention relates to compounds which are photolabile precursors of trehalose-6-phosphate and trehalose-6-phosphonate and salts thereof, as well as compositions containing the compounds, methods of treating plants with the compounds and the use of the compounds to increase starch production in plants.

Trehalose-6-phosphate is a sugar signalling molecule in plants and has significant effects on metabolism, growth and development. In most plants, trehalose is found in micromolar amounts, in contrast to sucrose which is present in millimolar amounts. This has led to the suggestion that the trehalose pathway is involved in signal transduction mechanisms in plants. This suggestion has been further confirmed in a range of mutants and transgenic plants.

A signalling partner of trehalose-6-phosphate is known to be SnRK1 of the AMPK/SNF1 group of protein kinases. A model for the function of trehalose-6-phosphate is that trehalose-6-phosphate responds to sucrose supply and, through inhibition of SnRK1, upregulates processes associated with growth, thus linking sucrose with downstream processes that use carbon. Trehalose-6-phosphate therefore has potent and beneficial effects on plant processes, in particular the regulation of sugar utilisation and starch metabolism. Trehalose-6-phosphate's importance in regulating plant metabolism and development makes it a significant target for the modification of crop yield.

Genetic approaches have previously been used to modify the trehalose pathway. For example, transgenic plants have been suggested which over express trehalose phosphate synthase (TPS), resulting in the formation of more trehalose-6-phosphate in plant. However, such genetic techniques have significant disadvantages and are not globally acceptable.

The present inventors, in contrast, have provided a chemical intervention approach for increasing the concentration of trehalose-6-phosphate or trehalose-6-phosphonate in plants. The present inventors have used a prodrug-type concept to provide compounds which are themselves typically biologically inert, but which are converted in planta to the active trehalose-6-phosphate or trehalose-6-phosphonate. Conversion to trehalose-6-phosphate or trehalose-6-phosphonate in the plant is achieved by photocleavage, either using applied radiation or sunlight. Treatment of plants with the compounds of the invention has been shown to cause release of trehalose-6-phosphate or trehalose-6-phosphonate in planta and lead to increased starch production.

Accordingly, the present invention provides the use of a compound which is a trehalose-6-phosphate or trehalose-6-phosphonate precursor of formula (I) or an agriculturally acceptable salt thereof, in increasing starch production in a plant:

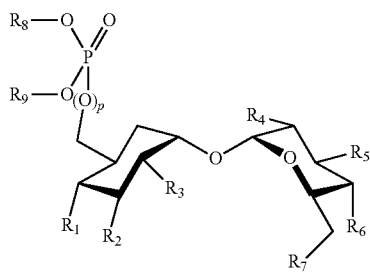

(I)

wherein:
p is 0 or 1;
$R_1$ to $R_7$ independently represent F, $N_3$, NR'R'', $C_{1-4}$alkyl, —($C_{1-4}$alkyl)OH or OH, wherein R' and R'' independently represent hydrogen or $C_{1-4}$alkyl; and
$R_8$ and $R_9$ are the same or different and represent H or a photolabile protecting group, wherein at least one of $R_8$ and $R_9$ represents a photolabile protecting group.

The present invention also provides a compound which is a trehalose-6-phosphate or trehalose-6-phosphonate precursor of formula (I) as defined herein or an agriculturally acceptable salt thereof.

Also provided is a composition comprising such a compound together with an agriculturally acceptable carrier or diluent, as well as the use of such a compound or composition in increasing crop yield. The compounds and compositions of the invention are also useful in reducing the incidence of pre-harvest sprouting of a crop.

The present invention also provides a method of increasing starch production in a plant, which method comprises treating the plant or the locus of the plant with an effective amount of a compound or composition of the invention. Also provided is a method of increasing crop yield, which method comprises treating the crop or the locus of the crop with an effective amount of a compound or a composition according to the invention. Also provided is a method of reducing the incidence of pre-harvest sprouting of a crop, which method comprises treating the crop, typically the harvestable part of the crop, or the locus of the crop with an effective amount of a compound or a composition according to the invention.

BRIEF DESCRIPTION OF THE FIGURES

FIG. 5 shows chromatograms generated in accordance with Example 9 below. Integration of the peak areas was used to determine the concentration of T6P in plant.

DETAILED DESCRIPTION OF THE INVENTION

Figure 1:
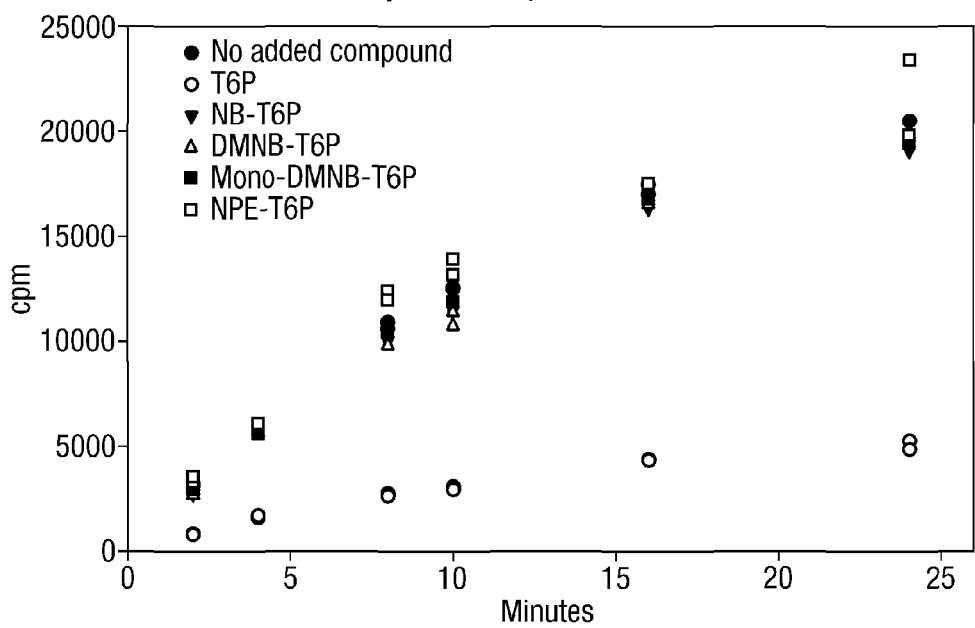
FIG. 1 provides the results of an SnRK1 assay carried out using Examples 1 to 4 as well as trehalose-6-phosphate for comparison.

As used herein a $C_{1-4}$ alkyl group or moiety is a straight or branched alkyl group or moiety containing from 1 to 4 carbon atoms, preferably from 1 to 2 carbon atoms. Examples of such groups include methyl, ethyl, n-propyl and i-propyl groups and moieties. An alkyl group or moiety is unsubstituted or substituted with one or more substituents, typically 1, 2 or 3 substituents, preferably 1 or 2 substituents. Suitable substituents are halogen atoms. Typically, alkyl groups and moieties are unsubstituted.

As used herein, halogen includes fluorine, chlorine and bromine.

As used herein, an aryl group includes phenyl and naphthyl.

As used herein, a heterocyclic group is a saturated, partially unsaturated or unsaturated, monocyclic or fused, 5- to 14-membered ring system in which the ring contains at least 1 heteroatom. Typically, the heterocyclic group is unsaturated or partially unsaturated, for example it may be unsaturated. Typically, the ring contains up to 3 or 4 heteroatoms, e.g. 1 or 2 heteroatoms, selected from O, S and N. Examples of suitable heterocyclic groups include pyridyl, furanyl, pyrrolyl, thiophenyl, oxazolyl, isoxazolyl, thiazolyl, pyrazolyl, imidazolyl, pyrimidinyl, pyrazinyl, pyridazinyl, indolyl, indolinyl, benzofuranyl, benzothiophenyl, benzimidazolyl, benzoxazolyl, benzopyrazolyl, benzothiazolyl, benzotriazolyl, quinolinyl, quinazolinyl, quinoxalinyl, carbazolyl, dibenzofuranyl and 9H-thioxanthene. Preferred examples include dibenzofuranyl, quinolinyl, indolinyl, and 9H-thioxanthene. In one aspect, the heterocyclic group may be a 5- or 6-membered saturated or partially unsaturated ring system. Examples of suitable 5- or 6-membered saturated or partially unsaturated heterocyclic groups include tetrahydrofuranyl, 1,3-dioxolanyl, pyrrolidinyl, 1,3-dioxolyl, dihydrofuranyl, imidazolyl, dihydropyrrolyl, dihydropyranyl and tetrahydropiperidinyl. Tetrahydrofuranyl, 1,3-dioxolanyl, dihydrofuranyl and 1,3-dioxolyl are preferred.

An aryl or heterocyclic group as used herein can be an aryl group or a 5- to 14-membered heterocyclic group having 1 or 2 ring carbon atoms being replaced with a group $>C(=O)$. Examples of such aryl and heterocyclic groups include coumarinyl and anthracene-9,10-dionyl.

An aryl group or a heterocyclic group may be unsubstituted or substituted. In the case of a heterocyclic group, substituents may be carried on a carbon atom in the ring or on a heteroatom in the ring. Typically, a heterocyclic or aryl group carries up to 3 substituents, e.g. 1 or 2 substituents. The heterocycle may be connected to the remainder of the molecule by a bond to any of its available ring positions.

Suitable substituents on an aryl or heterocyclic group include $C_{1-4}$ alkyl, —OR', halogen, CN, —NR'R", —COOR', —($C_{1-4}$alkyl)COOR' and —O($C_{1-4}$alkyl)COOR', wherein R' and R" are independently selected from hydrogen and $C_{1-4}$ alkyl. Alternatively, two adjacent substituents on the aryl or heterocyclic group may together form a 5- or 6-membered heterocyclic ring (i.e. a further ring fused to the aryl or heterocyclic group) containing one or more heteroatoms selected from N, O or S. For example, two adjacent substituents may form a —$CH_2$—O—$CH_2$— or —O—$CH_2$—O— moiety. Typically, no more than two, preferably no more than one, CN substituent is present on any aryl or heterocyclic ring.

As used herein and unless otherwise specified, the abbreviation T6P refers to both trehalose-6-phosphate and trehalose-6-phosphonate.

The compounds of the invention may be trehalose-6-phosphate precursors. In this case, p in formula (I) represents 1. Alternatively, the compounds may be trehalose-6-phosphonate precursors. In this case, p in formula (I) represents 0.

In one embodiment of the invention, $R_1$ to $R_7$ each represent hydroxyl. In this embodiment, on cleavage of the photolabile protecting group, trehalose-6-phosphate or trehalose-6-phosphonate will be provided.

In an alternative embodiment, one or more, preferably one, of $R_1$ to $R_7$ represents F, $N_3$, NR'R", $C_{1-4}$alkyl, or —($C_{1-4}$alkyl)OH, wherein R' and R" independently represent hydrogen or $C_{1-4}$alkyl. The remainder of $R_1$ to $R_7$ typically represent OH. In this embodiment, on cleavage of the photolabile protecting group, a modified trehalose-6-phosphate or trehalose-6-phosphonate compound will be produced. This embodiment provides the possibility of carrying out imaging studies, for example using a labelled trehalose-6-phosphate or phosphonate precursor in which one or more, preferably one, of $R_1$ to $R_7$ represents F. Such a precursor will release a labelled trehalose-6-phosphate or phosphonate in the plant.

Typically, $R_1$ to $R_7$ independently represent F, $N_3$, $NH_2$, methyl, ethyl, hydroxymethyl, hydroxyethyl or OH, for example $R_1$ to $R_7$ may independently represent F, $N_3$, $NH_2$, methyl or OH. It is preferred that at least 6 of $R_1$ to $R_7$ are the same and represent OH. Most preferably, all of $R_1$ to R are the same and represent OH.

The compounds of the invention may contain one or two photolabile protecting groups at positions $R_8$ and/or $R_9$. In one embodiment, two photolabile protecting groups are present at positions $R_8$ and $R_9$. These two photolabile protecting groups may optionally be bonded to one another to form a divalent photolabile protecting group, for example via position $R_{10}$ in formula (II) below. Where two photolabile protecting groups are present, these may be the same or different. For example, one of R8 and R9 may represent a photolabile group which is easily cleaved, whereas the other of R8 and R9 may represent a photolabile group which is cleaved more slowly. Typically, the two photolabile protecting groups are the same.

As used herein a photolabile protecting group is a group which is cleaved from the main part of the molecule when exposed to light, typically when exposed to sunlight. Preferably, the photolabile group is cleaved from the main part of the molecule when exposed to UV-Vis radiation having a wavelength in the range of from 100 nm to 800 nm, typically in the range of from 200 to 400 nm.

Photolabile groups are easily identifiable due to their activity when exposed to light. Suitable groups are identified, for example, by Mayer et al (Andew. Chem. Int. Ed. 2006, 45, 4900-4921) and Yu et al (Chem. Soc. Rev., 2010, 39, 464-473). A simple test can be carried out to confirm whether a group is a photolabile protecting group in accordance with the present invention. Such a test involves providing an aqueous solution of a compound of the invention containing a possible photolabile protecting group at position $R_8$ and/or $R_9$. The solution is then exposed to sunlight for a period of at least 5 hours, preferably 8 hours (or to UV light (200-400 nm) for a period of at least 15 minutes, preferably at least 30 minutes) and the appearance of T6P is monitored, for example by use of P NMR or mass spectrometry. Prior to sunlight exposure, little or no peak corresponding to T6P will be present in the P NMR or mass spectrum. Following exposure, however, if the group in question is a photolabile protecting group in accordance with the invention, a peak corresponding to T6P will be seen, since the photolabile group is removed during exposure to sunlight. The procedure is described in detail with reference to a number of particular compounds of the invention in Example 6 below.

An alternative test to determine whether a group is a photolabile group in accordance with the invention is to prepare a simple carboxylic acid derivative of the potential photolabile protecting group and to observe the release of the original carboxylic acid compound following photolysis. In particular, the potential photolabile protecting group can be bonded to o-chlorobenzoic acid by reaction of the potential photolabile protecting group having a hydroxy group at the cleavage point (e.g. X in formula (II) below) with 2-chlorobenzoic acid and DMAP in anhydrous dichloromethane (see Sing et al., Tetrahedron 61 (2005) 10007-10012). The resulting protected carboxylic acid can be subjected to photolysis (exposure to sunlight for at least five hours, preferably at least eight hours or to UV, wavelength 200-400 nm for at least 15 minutes, preferably at least 30 minutes) and the reappearance of the 2-chlorobenzoic acid compound can be observed, for example by HPLC analysis. Photolabile protecting groups in accordance with the invention will, when they undergo such a test, release the original 2-chlorobenzoic acid compound following photolysis.

In one embodiment of the invention, the photolabile protecting group is a group of formula (II), wherein X represents the position of attachment to the trehalose-6-phosphate or trehalose-6-phosphonate (T6P) group:

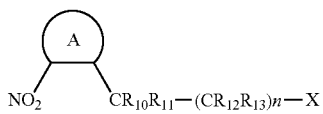
(II)

wherein
ring A represents an aryl or heterocyclic group;
either (i) $R_{10}$ and $R_{11}$ are the same or different and are selected from hydrogen, $C_{1-4}$ alkyl which is unsubstituted or substituted with one or more halogen atoms, —OR', halogen, —NR'R" or —CO$_2$R', wherein R' and R" are independently selected from hydrogen and $C_{1-4}$ alkyl, or (ii) two $R_{10}$ groups on adjacent photolabile protecting groups together form a bond and $R_{11}$ represents hydrogen, $C_{1-4}$ alkyl which is unsubstituted or substituted with one or more halogen atoms, —OR', halogen, —NR'R" or —CO$_2$R', wherein R' and R" are independently selected from hydrogen and $C_{1-4}$ alkyl;
n is 0 or 1; and
$R_{12}$ and $R_{13}$ are the same or different and are selected from hydrogen, $C_{1-4}$ alkyl which is unsubstituted or substituted with one or more halogen atoms, —OR', halogen, —NR'R" or —CO$_2$R', wherein R' and R" are independently selected from hydrogen and $C_{1-4}$ alkyl;
wherein X represents the link to the remainder of the compound of formula (I).

Typically, ring A represents a $C_{6-10}$ aryl group or a 5- to 14-membered heterocyclic group containing one or more atoms selected from N, O and S. Typically a heterocyclic group contains up to 4 heteroatoms, for example 1 or 2 heteroatoms, selected from N, O and S. Typically, the heterocyclic group is unsaturated or partially unsaturated, for example it may be unsaturated. Where ring A represents a heterocyclic group, the nitro group and —CR$_{10}$R$_{11}$ groups are typically each linked to a carbon atom on the ring. Ring A may be monocyclic or a fused ring system.

Preferred aryl groups are phenyl and naphthyl. A preferred heterocyclic group is dibenzofuranyl. Ring A is preferably a phenyl, naphthyl or dibenzofuranyl group, in particular a phenyl group.

Ring A may be unsubstituted or it may carry one or more substituents, for example 1, 2 or 3 substituents. Substituents on a heterocyclic group are typically carried on a carbon atom. Suitable substituents include $C_{1-4}$ alkyl, —OR', halogen, CN, —NR'R", —COOR', —(C$_{1-4}$alkyl)COOR' and —O(C$_{1-4}$alkyl)COOR', wherein R' and R" are independently selected from hydrogen and $C_{1-4}$ alkyl. Alternatively, two adjacent substituents on the aryl or heterocyclic group may together form a 5- or 6-membered heterocyclic ring (i.e. a further fused ring) containing one or more heteroatoms selected from N, O or S. For example, two adjacent substituents may form a —CH$_2$—O—CH$_2$— or —O—CH$_2$—O— moiety.

Preferably ring A is unsubstituted or carries one or two substituents selected from —OR', Br, —NR'R", —COOR', —(C$_{1-2}$alkyl)COOR' and —O(C$_{1-2}$alkyl)COOR', wherein R' and R" are independently selected from hydrogen and $C_{1-2}$ alkyl, or two adjacent ring positions are substituted with a —CH$_2$—O—CH$_2$— or —O—CH$_2$—O— moiety. More preferably, ring A is unsubstituted or carries one or two methoxy groups, or two adjacent ring positions are substituted with a —CH$_2$—O—CH$_2$— moiety. The substituents are themselves typically unsubstituted groups or moieties.

In one aspect, $R_{10}$ and $R_{11}$ are the same or different and are selected from hydrogen; $C_{1-4}$ alkyl which is unsubstituted or substituted with one or more halogen atoms; —OR'; halogen; —NR'R"; or —CO$_2$R'; wherein R' and R" are independently selected from hydrogen and $C_{1-4}$ alkyl.

Preferably, $R_{10}$ represents hydrogen, methyl, ethyl, CF$_3$, or —CO$_2$H. Preferably, $R_{11}$ represents hydrogen.

In an alternative aspect, two $R_{10}$ groups on adjacent photolabile protecting groups together form a bond. In this aspect, $R_{11}$ preferably represents hydrogen.

n is preferably 0.

Where present, $R_{12}$ and $R_{13}$ typically represent hydrogen.

Preferred photolabile protecting groups of formula (II) are groups of formula (IIa):

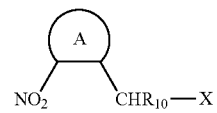
(IIa)

wherein
ring A represents an unsubstituted or substituted group selected from phenyl, naphthyl or dibenzofuranyl, wherein a substituted phenyl, naphthyl or dibenzofuranyl group is a phenyl, naphthyl or dibenzofuranyl group having one or two methoxy substituents, or a phenyl, naphthyl or dibenzofuranyl group wherein two adjacent ring positions are substituted with a —CH$_2$—O—CH$_2$— moiety; and $R_{10}$ represents hydrogen, methyl, —CF$_3$ or —COOH;

wherein X represents the link to the remainder of the compound of formula (I).

Specific examples of photolabile protecting groups of formula (II) are:

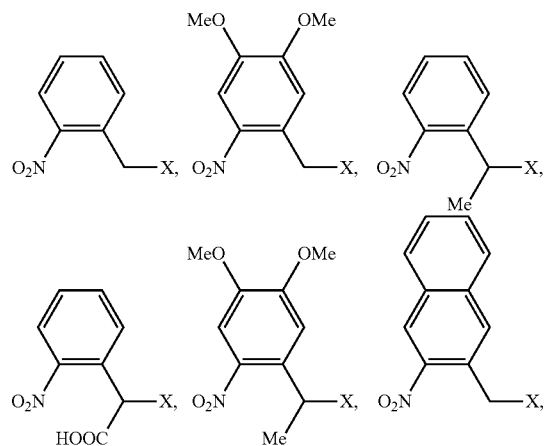

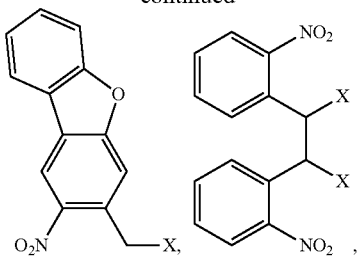

wherein X represents a bond to position $R_8$ and/or $R_9$ of the compound of formula (I).

In an alternative embodiment, the photolabile protecting group is of formula (III):

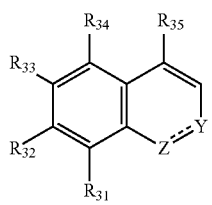

wherein
either Z represents N, Y represents $CR_{36}$ and Z and Y are linked by a double bond; or
Z represents O, Y represents C=O and Z and Y are linked by a single bond;
$R_{36}$ represents —$CR_{37}R_{38}X$;
when Y represents $CR_{36}$, $R_{35}$ represents hydrogen, and when Y represents C=O, $R_{35}$ represents —$CR_{37}R_{38}X$;
either (i) $R_{37}$ and $R_{38}$ are the same or different and are selected from hydrogen, $C_{1-4}$ alkyl which is unsubstituted or substituted with one or more halogen atoms, —OR', halogen, —NR'R" or —$CO_2R'$ wherein R' and R" are independently selected from hydrogen and $C_{1-4}$ alkyl, or (ii) two $R_{37}$ groups on adjacent photolabile protecting groups together form a bond and $R_{38}$ represents hydrogen, $C_{1-4}$ alkyl which is unsubstituted or substituted with one or more halogen atoms, —OR', halogen, —NR'R" or —$CO_2R'$ wherein R' and R" are independently selected from hydrogen and $C_{1-4}$ alkyl;
$R_{32}$ represents —OR', —NR'R", —O($C_{1-4}$alkyl)-COOR', —O($C_{1-4}$alkyl)-OR' or —O($C_{1-4}$alkyl)-NR'R", wherein R' and R" independently represent hydrogen or $C_{1-4}$ alkyl; and
$R_{31}$, $R_{33}$ and $R_{34}$ are independently selected from hydrogen, halogen, —OR', —NR'R", —O($C_{1-4}$alkyl)-COOR', —O($C_{1-4}$alkyl)-OR' or —O($C_{1-4}$alkyl)-NR'R", wherein R' and R" independently represent hydrogen or $C_{1-4}$ alkyl;
wherein X represents the link to the remainder of the compound of formula (I).

In the photolabile protecting group of formula (III), in one aspect Z represents O, Y represents C=O and Z and Y are linked by a single bond, such that the ring structure is a coumarin ring. In this aspect, $R_{35}$ represents —$CR_{37}R_{38}X$, wherein X is a bond to the remainder of formula (I).

In an alternative aspect, Z represents N, Y represents C—$CR_{37}R_{38}X$ and Z and Y are linked by a double bond, such that the ring structure forms a quinoline ring. In this aspect, $R_{35}$ represents hydrogen.

Typically, $R_{37}$ and $R_{38}$ are the same or different and are selected from hydrogen, $C_{1-4}$ alkyl which is unsubstituted or substituted with one or more halogen atoms, —OR', halogen, —NR'R" or —$CO_2R'$, wherein R' and R" are independently selected from hydrogen and $C_{1-4}$ alkyl; or $R_{38}$ is hydrogen and two $R_{37}$ groups on adjacent photolabile protecting groups together form a bond.

Preferably, $R_{37}$ represents hydrogen, methyl, ethyl, $CF_3$, or —$CO_2H$. More preferably, $R_{37}$ represents hydrogen. Preferably, $R_{38}$ represents hydrogen, methyl, ethyl, $CF_3$, or —$CO_2H$. More preferably, $R_{38}$ represents hydrogen.

Typically, $R_{32}$ represents —OR', —NR'R" or —O($C_{1-2}$alkyl)-COOR', wherein R' and R" independently represent hydrogen or $C_{1-2}$ alkyl. Preferably, $R_{32}$ represents —OR', —NR'R" or —O($CH_2$)—COOH, wherein R' and R" independently represent hydrogen or $C_{1-2}$ alkyl.

Typically, $R_{31}$, $R_{33}$ and $R_{34}$ are independently selected from hydrogen, Br, —OR', —NR'R" or —O($C_{1-2}$alkyl)-COOR', wherein R' and R" independently represent hydrogen or $C_{1-2}$ alkyl. Preferably, $R_{31}$ is hydrogen or Br. Preferably, $R_{33}$ is hydrogen, Br or —$OCH_2CO_2H$. Preferably, $R_{34}$ is hydrogen.

Preferably, the photolabile group of formula (III) is a group of formula (IIIa):

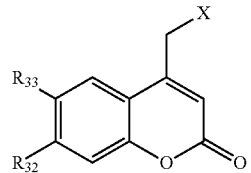

wherein
$R_{32}$ represents —OR', —NR'R", —O($C_{1-4}$alkyl)-COOR', —O($C_{1-4}$alkyl)-OR' or —O($C_{1-4}$alkyl)-NR'R", wherein R' and R" independently represent hydrogen or $C_{1-4}$ alkyl; and
$R_{33}$ represents hydrogen, halogen, —OR', —NR'R", —O($C_{1-4}$alkyl)-COOR', —O($C_{1-4}$alkyl)-OR' or —O($C_{1-4}$alkyl)-NR'R", wherein R' and R" independently represent hydrogen or $C_{1-4}$ alkyl;
wherein X represents the link to the remainder of the compound of formula (I).

In the groups of formula (IIIa), preferably $R_{32}$ represents —OR', —NR'R" or —O($C_{1-4}$alkyl)-COOR', wherein R' and R" independently represent hydrogen or $C_{1-2}$ alkyl; and $R_{33}$ represents hydrogen, Br, —OR', —NR'R" or —O($C_{1-4}$alkyl)-COOR', wherein R' and R" independently represent hydrogen or $C_{1-2}$ alkyl.

Specific examples of photolabile protecting groups of formula (IIIa) are those wherein:

a) $R_{33}$ represents H and $R_{32}$ represents OMe, $NMe_2$, $NEt_2$ or —$OCH_2COOH$;

b) $R_{33}$ represents Br and $R_{32}$ represents OH; and c) $R_{33}$ and $R_{32}$ both represent —$OCH_2COOH$.

Alternatively, the photolabile protecting group of formula (III) may be a group of formula (IIIb):

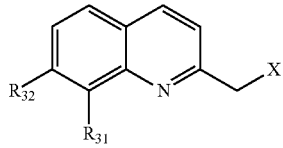
(IIIb)

wherein $R_{31}$ and $R_{32}$ are as described above for formula (III).

In the groups of formula (IIIb), preferably $R_{32}$ represents —OR', —NR'R" or —O($C_{1-4}$alkyl)-COOR', wherein R' and R" independently represent hydrogen or $C_{1-2}$ alkyl; and $R_{31}$ represents hydrogen, Br, —OR', —NR'R" or —O($C_{1-4}$alkyl)-COOR', wherein R' and R" independently represent hydrogen or $C_{1-2}$ alkyl.

A specific example of a photolabile protecting group of formula (IIIb) is a group wherein $R_{31}$ represents Br and $R_{32}$ represents OH.

Further alternative photolabile protecting groups which can be used at positions $R_8$ and/or $R_9$ in the compounds of the invention include:

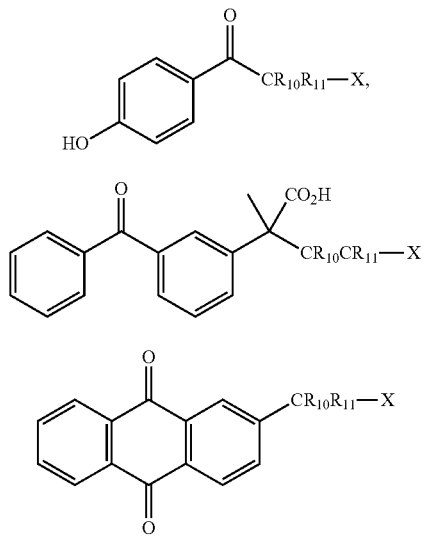

IVa

IVb

IVc wherein $R_{10}$ and $R_{11}$ are as defined above for formula (II). In the compounds of formulae (IVa), (IVb) and (IVc), preferably $R_{10}$ and $R_{11}$ are hydrogen. Specific examples include:

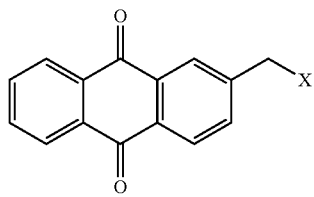

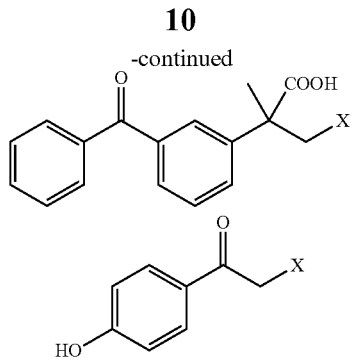

Alternative photolabile protecting groups are those described in Mayer et al (Andew. Chem. Int. Ed. 2006, 45, 4900-4921) and Yu et al (Chem. Soc. Rev., 2010, 39, 464-473). Particular examples include

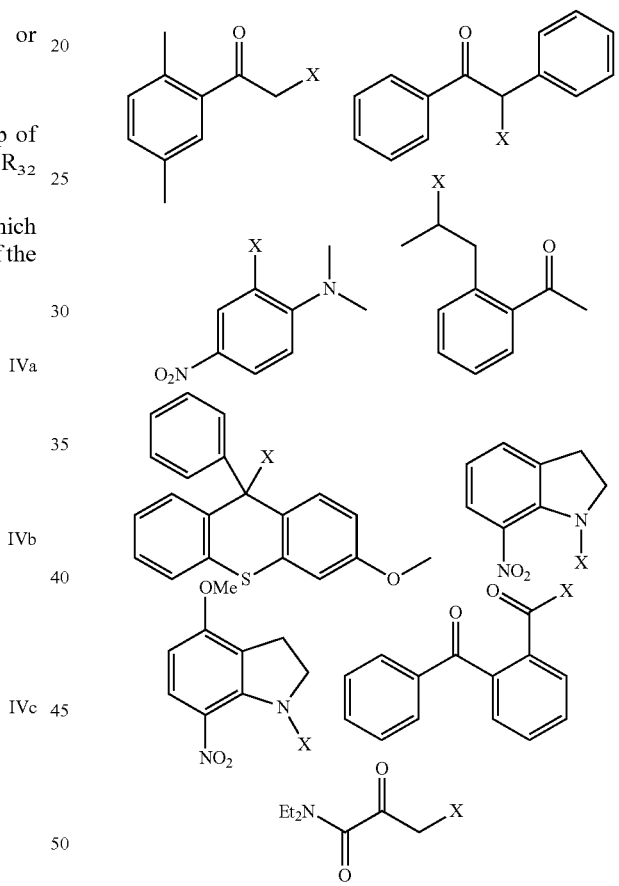

Compounds used in the invention are derivatives of D-trehalose (α-D-glucopyranosyl-[1,1]-α-D-glucopyranoside, i.e. α,α-1,1 linkage) and are preferably used in enantiomerically pure form. However, they may be present as a mixture of isomers, for example a mixture containing one or more derivatives of α-D-glucopyranosyl-[1,1]-β-D-glucopyranoside, β-D-glucopyranosyl-[1,1]-α-D-glucopyranoside and β-D-glucopyranosyl-[1,1]-β-D-glucopyranoside. Typically, where a mixture of isomers is present, the α,α form is present in an amount of at least 60 wt %, preferably at least 70 wt %. For the avoidance of doubt, the compounds used in the invention may be used in any tautomeric form. Further, for the avoidance of doubt, the compounds of the invention may be used in the form of a solvate or hydrate.

Suitable agriculturally acceptable salts of the compounds of the invention include salts with agriculturally acceptable bases such as alkali metal (e.g. sodium or potassium) and alkaline earth metal (e.g. calcium or magnesium) hydroxides and organic bases such as alkyl amines, aralkyl amines or heterocyclic amines. Where appropriate, salts may also be formed with agriculturally acceptable acids, both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid.

The compounds of the invention wherein $R_1$ to $R_7$ are OH, p=1 and $R_8$ and $R_9$ are identical may be synthesised in accordance with the following schemes 1 and 2:

Scheme 1

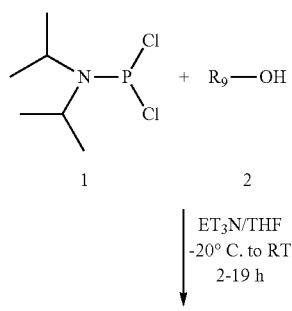

1    2

ET₃N/THF
-20° C. to RT
2-19 h

-continued

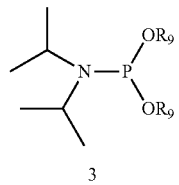

3

Phosphoramidite compounds 3 may be produced from diisopropyl phosphoramidous chloride 1, by treatment of 1.0 equivalent of diisopropyl phosphoramidous chloride 1 with 2.0 equivalents of compound 2 in dry THF using triethylamine as a base at −20° C. to room temperature.

The produced phosphoramidite compounds 3 can be converted to compounds of formula (I) in accordance with scheme 2:

Scheme 2

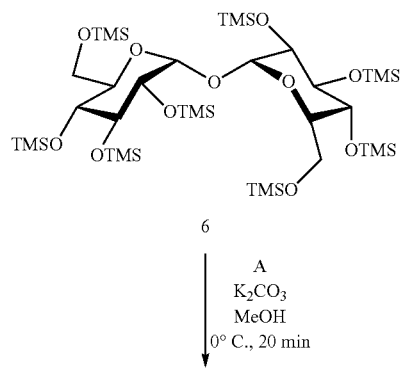

6

A
K₂CO₃
MeOH
0° C., 20 min

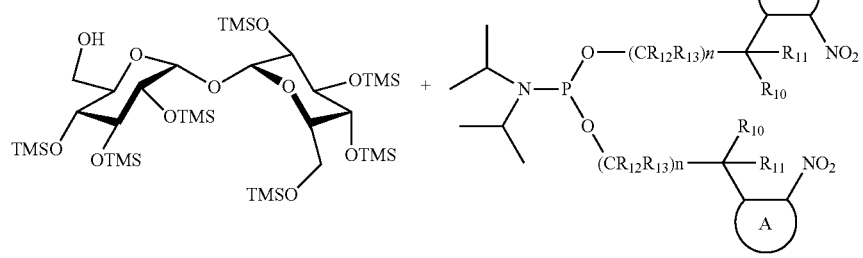

4    3

B
i) tetrazole soln, CH₂Cl₂, 0-5° C., 2-18 h
ii) tBuOOH, 30 min
iii) Dowex-H⁺, MeOH, RT, 1 h, 43-87%

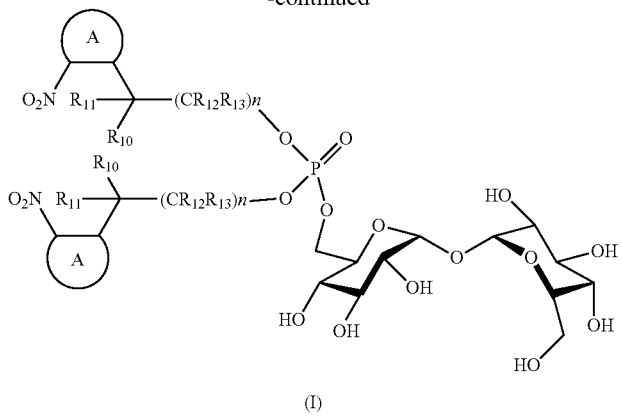

(I)

2,3,4,2',3',4',6'-heptakis-O-(trimethylsilyl)-D-trehalose 4 can be prepared by regioselective deprotection of persilylated D-trehalose 6 under acidic conditions (Ronnow et al, Carbohydr. Res. 260, 323-328 (1994)). Partially deprotected trehalose 4 can then be reacted with compound 3 as set out in scheme 2, yielding the compounds of the invention.

In an alternative approach, step B of scheme 2 may be carried out by treating 4 with 1.0 equiv. of POCl$_3$ in pyridine for 10 minutes followed by the addition of 2.0 equivalents of compound 2 and stirring for 1 hour. This alternative approach leads to a mixture of mono- and di-substituted phosphates as shown in scheme 3:

substituted compounds with a further photolabile reacting group R$_8$OH to provide a compound of the invention having different photolabile protecting groups R$_8$ and R$_9$.

Compounds of the invention wherein p=0, i.e. compounds having a phosphonate group, can be prepared by adopting the Michaelis-Arbuzov reaction on substrate 7 (see scheme 4 below). Substrate 7 can easily be prepared from halogenated trehalose as per literature procedure (*Nat. Chem. Biol.* 2011, 7, 228 and ref cited therein). The appropriate tri-O-alkyl phosphate compounds type 9 can be treated with substrate 7 under thermal or microwave conditions which results in the formation of the C—P bond. This is followed by the removal

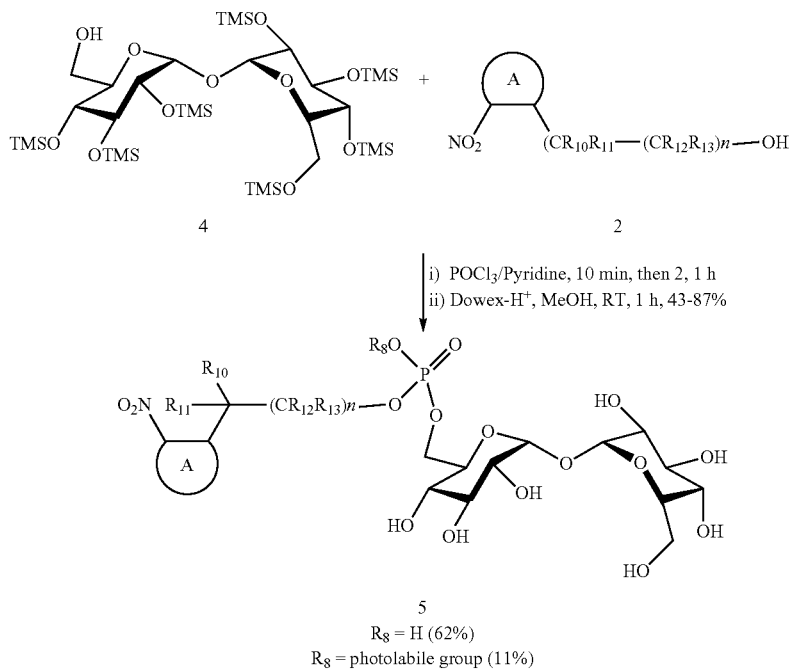

The starting materials 1, 2 and 6 are commercially available or can be prepared by standard techniques.

The compounds of the invention wherein R$_8$ and R$_9$ are different photolabile protecting groups can be prepared by following scheme 3 above and further reacting the monoof OTMS groups to give compound (I). In an alternative approach the compound of invention can also be prepared starting from substrate 7 by the reaction of an appropriate di-O-alkyl phosphite reagent type 8 in the presence of Pd-catalyst viz. Pd(PPh$_3$)$_4$ or Pd(OAc)$_2$ (*Org. Lett.* 2008, 10, 4637 and *Synlett.* 2009, 225)

In the case where $R_8$ or $R_9$ is H, compounds 8 and 9 are modified by replacing the hydrogen atom at $R_8$ or $R_9$ with a suitable protecting group prior to reaction. The protecting group can then be removed to yield compounds of formula (I).

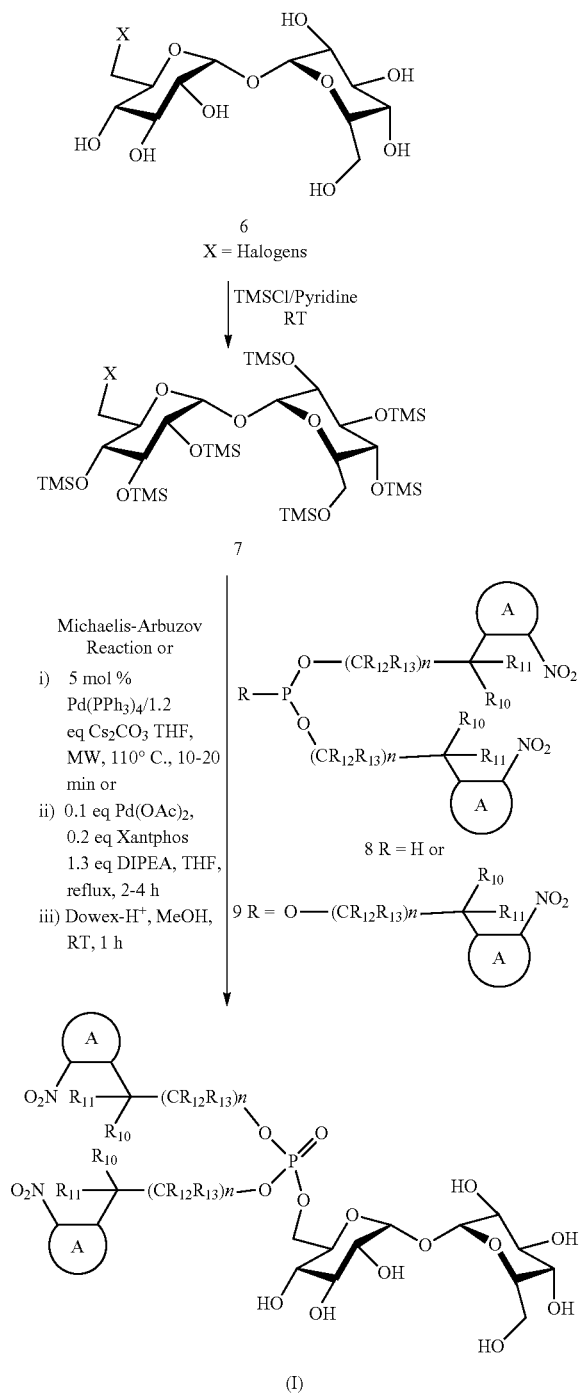

Compounds of the invention having a group other than OH at one or more of positions $R_1$ to $R_7$ can be prepared by processes analogous to those set out in schemes 1 to 4 above, but using as a starting material an appropriately modified trehalose. Trehalose which is modified at positions $R_1$ to $R_7$ are commercially available or could be produced using techniques which are routine in the art.

In use, the compounds of the invention are applied to the plant or crop or to the locus of the plant or crop. This may be done, for example, by application to the seeds of the plants or crop prior to sowing, to the medium (e.g. soil or water) in which the plants or crop are grown, to the foliage of the plants or crop, or to the parts of the plant or crop which will be harvested, e.g. seeds, fruit, tubers. Application to the harvestable parts of the plant or crop may be used to prevent or reduce the incidence of pre-harvest sprouting of seed (a common problem for cereals during wet weather during the harvest period) by preventing starch breakdown that occurs during pre-harvest sprouting.

The compounds of the invention are typically provided to the plant in the form of an aqueous solution. However, granules, powders or dust formulations are also envisaged. The compounds may therefore be provided in solid form, for example as granules, powder or dust either for direct application or together with instructions for making up a suitable solution at the time of use. Alternatively, the compounds of the invention may be provided as an aqueous solution, either a ready to use solution, or a concentrate which can be diluted prior to use. A ready to use solution will typically have a concentration of the compound of the invention in the range of 0.1 to 10 mM. A concentrate may have a higher concentration of the compound of the invention, for example at least 100 mM and up to 10M.

The present invention includes a composition comprising a compound of the invention, or an agriculturally acceptable salt thereof, and an inert, agriculturally acceptable carrier or diluent. Where a diluent is used, water is preferred.

Where the compound is provided as a powder, this may comprise the compound of the invention alone, or the compound may be provided in an intimate, finely divided mixture of a compound of the invention, an inert solid carrier and, if desired, a surface-active agent. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in proportions of from 0.5 to 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Solid compositions such as powders containing a compound of the invention desirably contain at least 0.1 percent, e.g. from 0.1 to 95 percent by weight of the compound of the invention and from 0.1 to 75 percent of an inert carrier or surfactant.

When a compound of the invention is to be applied to the soil, granular formulations or dusts are sometimes more convenient than sprays. A typical granular formulation comprises a compound of the invention dispersed on an inert carrier such as coarsely ground clay, or clay which has been converted to granules by treatment of a rolling bed of the powdered material with a small amount of liquid (e.g. water) in a granulating drum. In the usual process for preparing granular formulations, a solution of the active compound is sprayed on the granules while they are being agitated in a suitable mixing apparatus, after which the granules are dried with a current of air during continued agitation.

The compounds of the invention may be combined with other active ingredients used for the treatment of plants, for example they may be incorporated into other agrochemical products. For example, the compounds of the invention may be used in combination with fertilisers, anti-fungal agents and pesticides. For example, the compounds of the invention may be incorporated into fertiliser compositions or plant feed compositions.

The compounds of the invention are suitable for application to any plant. Suitable plants to which the compounds of the invention can be applied include the crop plants monocots and dicots such as corn, *brassica*, alfalfa, rice, sunflower, cotton, safflower, sorghum, wheat, tobacco, millet, soybean, potato, sugar beets, sugarcane, oats and barley, as well as vegetables, ornamental plants, grasses and trees including conifers. Plants treated with the compounds of the invention may have increased T6P levels and will also have elevated levels of cleaved photolabile protecting groups compared with untreated plants. Plants treated with the compounds of the invention accordingly produce greater amounts of starch than untreated plants. This may lead to increased plant growth and accordingly improved crop yields.

The compounds of the invention are particularly suitable for application to seed and stem crops, including potato crops. Preferred plants to which the compounds of the invention can be applied accordingly include corn, *brassica*, alfalfa, rice, sunflower, safflower, sorghum, wheat, millet, soybean, potato, sugar beets, sugarcane, oats and barley, as well as seed and stem crop vegetables.

EXAMPLES

The invention will now be described with reference to a number of specific examples, but the invention is not intended to be limited to these examples. In Examples 1 to 10 and FIGS. 1 to 6, the abbreviation T6P refers to trehalose-6-phosphate.

Reference Example 1 bis-(2-nitrobenzyl)-N,N-diisopropylphosphoramidite

Diisopropylphosphoramidous dichloride (2.0 g, 9.90 mmol) was dissolved in 15 mL of THF and the resulting solution was added slowly to a solution containing 4.2 mL (29.7 mmol) of triethylamine and 3.03 g (19.8 mmol) of 2-nitrobenzyl alcohol in 10 mL of THF at 0° C. The reaction mixture was stirred at 0° C. for 30 min and then at 25° C. for another 2 h. The colorless precipitate was isolated by filtration and the solid was washed with 100 mL of ethyl acetate. The organic phase was washed successively with 15 mL portions of saturated NaHCO$_3$ and saturated NaCl and then dried (MgSO4) and concentrated under diminished pressure at 25° C. The residue was precipitated from ethyl acetate/hexane, affording bis(2-nitrobenzyl)N,N-diisopropylphosphoramidite (3.0 g, 70%) as a colorless solid.

Reference Example 2 bis-(4,5-dimethoxy-2-nitrobenzyl)-N,N-diisopropylphosphoramidite

To a −20° C. cooled suspension of 4,5-dimethoxy-2-nitrobenzyl alcohol (2.1 g, 9.90 mmol) and triethylamine (1.5 mL, 10.8 mmol) in dry THF (10 mL) was added dropwise a solution of diisopropylphosphoramidous dichloride (1.0 g, 4.95 mmol) in dry THF (2 mL). The mixture was allowed to warm to 20° C., stirred for 18 h, and a saturated solution of aq. NaHCO$_3$, (15 mL) added. The solid was filtered, washed with water (20 mL) and dried to give 2.0 g (74%) of bis-(4,5-dimethoxy-2-nitrobenzyl)-N,N-diisopropylphosphoramidite.

Reference Example 3 bis-[1-(2-nitrophenyl)-ethyl]-N,N-diisopropylphosphoramidite

Diisopropylphosphoramidous dichloride (1.0 g, 4.95 mmol) was dissolved in 5 mL of dry THF and the resulting solution was added slowly to a solution containing 1.5 mL (10.89 mmol) of triethylamine and 1.65 g (9.90 mmol) of 1-methyl-2-nitrobenzyl alcohol in 10 mL of THF at 0° C. The reaction mixture was stirred at 0° C. for 1 min and then at 25° C. for another 18 h. The reaction mixture was diluted with EtOAc. The organic phase was washed successively with 15 mL portions of saturated NaHCO$_3$ and saturated NaCl and then dried (MgSO4) and concentrated under reduced pressure at 25° C. to get crude product. The residue was purified by flash column chromatography using ethyl acetate/petroleum ether (5:95 v/v), affording bis-[1-(2-nitrophenyl)-ethyl]-N, N-diisopropylphosphoramidite (1.6 g, 72%) as a colorless solid. Isolated in diastereomeric mixture form.

Example 1

NB-T6P

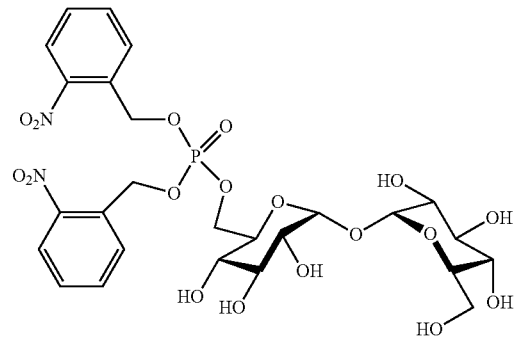

To a solution of 2,3,4,2',3',4',6'-heptakis-O-(trimethylsilyl)-D-trehalose (50 mg, 0.06 mmol, 1 equiv.) and 1H-tetrazol (8.4 mg, 0.12 mmol, 2.0 equiv.) in dry CH$_2$Cl$_2$ (3 mL) under an argon atmosphere at 0° C., bis-(2-nitrobenzyl)-N,N-diisopropylphosphoramidite prepared in Reference Example 1 (39.1 mg, 0.09 mmol, 1.5 equiv.) was added. The solution was stirred for 30 min and progress of the reaction was monitored by TLC (petroleum ether:ether; 8:2) and mass spectrometery. After complete disappearance of starting material, m-CPBA (20.7 mg, 0.12 mmol, 2.0 equiv) was added at 0° C. After 10 min the mixture was diluted with EtOAc (15 mL) and washed with saturated NaHCO$_3$ (2×5 mL) and saturated NaCl (3×5 mL) solutions. The organic layer was dried over MgSO$_4$, concentrated in vacuo and the residue was stirred using 30 mg of Dowex in methanol for 1 h to obtained deprotected compounds. After filtration the filtrate was concentrated to get fully deprotected crude product which on flash chromatography purification yielded NB-T6P (30 mg) in 75% isolable yield.

Example 1

$[\alpha]_D$ +80.6 (c 1.0, MeOH), $^1$HNMR (400 MHz, CD$_3$OD) δ 8.02 (d, J=8.0 Hz, 2H, ArH), 7.66-7.65 (m, 4H, ArH), 7.50-

7.46 (m, 2H, ArH), 5.43 (d, J=7.2 Hz, 4H, 2×CH$_2$), 4.96 (d, J=3.6 Hz, 1H, H-1), 4.93 (d, J=3.6 Hz, 1H, H-1'), 4.29-4.24 (m, 2H, H-6), 3.93 (td, J=8.4 Hz and J=2.0 Hz, 1H), 3.73-3.65 (m, 4H), 3.58 (dd, J=12.0 Hz and J=5.2 Hz, 1H), 3.36-3.33 (m, 2H), 3.30-3.20 (m, 3H); $^{13}$C NMR (100 MHz, CD$_3$OD) δ 147.7, 134.3, 132.1, 132.0, 129.4, 129.0, 128.9, 125.0, 94.4, 94.3, 73.5, 73.3, 72.8, 72.1, 72.0, 71.0, 70.9, 70.8, 70.1, 66.6, 61.6; $^{31}$P NMR (162 MHz, CD$_3$OD) δ −1.65; ESI-HRMS m/z calculated for C$_{26}$H$_{33}$N$_2$O$_{18}$P [M+Na]$^+$: 715.1368; Found 715.1368.

Example 2

DMNB-T6P

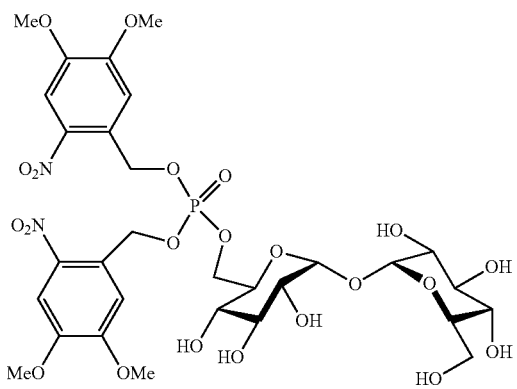

To a solution of 2,3,4,2',3',4',6'-heptakis-O-(trimethylsilyl)-D-trehalose (100 mg, 0.12 mmol, 1 equiv.) and 1H-tetrazol (210 mg, 3.0 mmol, 25 equiv.) in dry CH$_3$CN (5 mL) under an argon atmosphere at 0° C., bis-(4,5-dimethoxy-2-nitrobenzyl)-N,N-diisopropylphosphoramidite prepared in Reference Example 2 (100 mg, 0.18 mmol, 1.5 equiv.) was added. The solution was stirred for 30 min and progress of the reaction was monitored by TLC (petroleum ether:ether; 8:2) and mass spectrometery. After complete disappearance of starting material, m-CPBA (41.5 mg, 0.24 mmol, 2.0 equiv) was added at 0° C. After 10 min the mixture was diluted with EtOAc (10 mL) and washed with saturated NaHCO$_3$ (2×5 mL) and saturated NaCl (3×5 mL) solutions. The organic layer was dried over MgSO$_4$, concentrated in vacuo to obtained residue mixture. Thus residue mixture was deprotected by simple stirring using 25 mg of Dowex in methanol for 1 h. After filtration the filtrate was concentrated to get fully deprotected crude product which on flash chromatography purification yielded DMNB-T6P (29 mg) in 30% isolable yield along with trehalose.

Example 2

[α]$_D$ +64.8 (c 1.1, MeOH), $^1$HNMR (400 MHz, CD$_3$OD) δ 7.53 (s, 2H, ArH), 7.03 (s, 2H, ArH), 5.37 (d, J=8.0 Hz, 4H, 2×CH$_2$), 4.95 (d, J=4.0 Hz, 1H, H-1), 4.91 (d, J=4.0 Hz, 1H, H-1'), 4.33-4.28 (m, 2H, H-6), 3.94 (td, J=10.0 Hz and J=2.0 Hz, 1H), 3.81 (s, 6H, 2×OCH$_3$), 3.78 (s, 6H, 2×OCH$_3$), 3.73-3.65 (m, 4H), 3.58 (dd, J=12.0 Hz and J=5.2 Hz, 1H), 3.35 (dd, J=8.4 Hz and J=4.0 Hz, 1H), 3.32 (dd, J=6.0 Hz and J=2.0 Hz, 1H), 3.26-3.31 (m, 3H); $^{13}$C NMR (100 MHz, CD$_3$OD) δ 154.2, 148.9, 143.7, 139.6, 126.8, 126.6, 110.4, 110.3, 108.2, 94.4, 94.3, 73.5, 73.3, 72.8, 72.1, 72.0, 70.8, 70.2, 65.4, 61.6, 56.1, 55.8; $^{31}$P NMR (162 MHz, CD$_3$OD) δ −1.67; ESI-HRMS m/z calculated for C$_{30}$H$_{41}$N$_2$O$_{22}$P [M+Na]$^+$: 835.1786; Found 835.1782.

Example 3

NPE-T6P

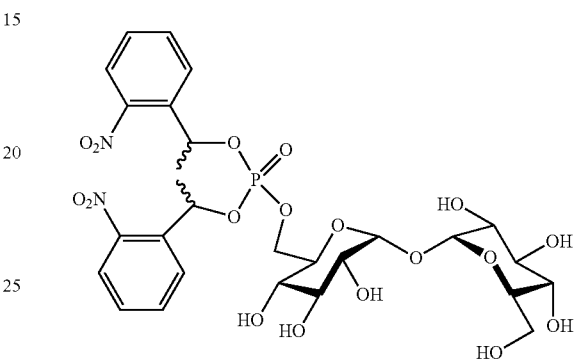

To a solution of 2,3,4,2',3',4',6'-heptakis-O-(trimethylsilyl)-D-trehalose (100 mg, 0.12 mmol, 1 equiv.) and 1H-tetrazol (84 mg, 1.2 mmol, 10 equiv.) in dry CH$_2$Cl$_2$ (5 mL) under an argon atmosphere at 0° C., bis-[1-(2-nitrophenyl)-ethyl]-N,N-diisopropylphosphoramidite prepared in Reference Example 3 (83.5 mg, 0.18 mmol, 1.5 equiv.) was added. The solution was stirred for 30 min and progress of the reaction was monitored by TLC (petroleum ether:ether; 8:2) and mass spectrometry.

After complete disappearance of starting material, t-BuOOH (0.1 mL, 0.36 mmol, 3.0 equiv) was added at 0° C. After 10 min the mixture was diluted with EtOAc (10 mL) and washed with saturated NaHCO$_3$ (2×5 mL) and saturated NaCl (3×5 mL) solutions. The organic layer was dried over MgSO$_4$, concentrated in vacuo to obtained residue mixture. Thus residue mixture was deprotected by simple stirring using 25 mg of Dowex in methanol for 1 h. After filtration the filtrate was concentrated to get fully deprotected crude product which on flash chromatography purification yielded NPE-T6P (40 mg) in 47% isolable yield along with trehalose.

Example 3

$^1$HNMR (400 MHz, CD$_3$OD) δ 7.91-7.05 (m, 8 H, ArH), 5.92-5.84 (m, 2H, CHMe), 5.04-4.94 (m, 2H, H-1 and H-1'), 4.16-3.99 (m, 2H, CHMe$_2$), 3.90-3.60 (m, 7H), 3.41-3.05 (m, 5H), 1.56-1.46 (m. 6H, CH$_3$); $^{13}$C NMR (125 MHz, CD$_3$OD) δ 148.8, 148.3, 148.2, 148.1, 147.9, 145.4, 138.9, 238.3, 138.2, 135.4, 135.3, 135.2, 130.4, 130.3, 129.9, 129.3, 129.2, 128.8, 128.7, 128.6, 126.3, 125.6, 125.5, 95.4, 95.3, 79.8, 74.6, 74.4, 74.2, 73.9, 73.8, 73.1, 73.0, 71.8, 71.1, 68.3, 62.6, 62.1, 59.8, 30.7, 30.5, 24.7, 24.6. 23.5, 23.4 23.7; $^{31}$P NMR (162 MHz, CD$_3$OD) δ −3.64, −3.96; ESI-HRMS m/z calculated for C$_{28}$H$_{37}$N$_2$O$_{18}$P [M+Na]$^+$: 743.1677; Found 743.1676.

Example 4

Mono-DMNB-T6P

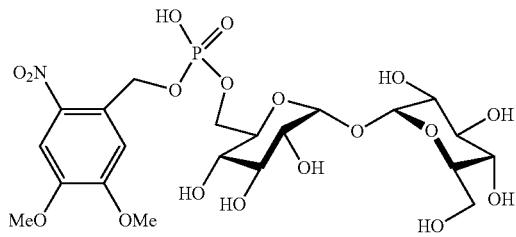

To a stirred solution of 2,3,4,2',3',4',6'-heptakis-O-(trimethylsilyl)-D-trehalose (100 mg, 0.12 mmol) in pyridine (2 mL) at room temperature, $POCl_3$ (0.012 mL, 0.132 mmol) was added and stirred for 10 min. After 10 min 4,5-dimethoxy-2-nitrobenzyl alcohol (76.7 mg, 0.36 mmol) was added and the reaction mixture stirred at the same temperature for 1 h. The reaction mixture was concentrated in vacuo to get crude product mixture, which after treatment with Dowex (50 mg) in methanol (2 mL) furnished a mixture of DMNB-T6P (Example 2) and mono-DMNB-T6P (Example 4). After filtration, concentration in vacuo and flash chromatography purification yielded DMNB-T6P (10 mg, 11%) and Mono-DMNB-T6P (45 mg, 62%) as a pure sticky solid.

Example 4

$[\alpha]_D$ +48.7 (c 1.1, MeOH), $^1$HNMR (400 MHz, $CD_3OD$) δ 7.62 (s, 1H, ArH), 7.39 (s, 1H, ArH), 5.21 (d, J=6.0 Hz, 2H, $CH_2$), 4.91 (d, J=4.0 Hz, 1H, H-1), 4.87 (d, J=4.0 Hz, 1H, H-1'), 4.00-3.98 (m, 2H, H-6), 3.88 (s, 3H, $OCH_3$), 3.80 (s, 3H, $OCH_3$), 3.71-3.65 (m, 4H), 3.57 (dd, J=12.0 Hz and J=5.6 Hz, 1H), 3.35 (dd, J=7.2 Hz and J=3.6 Hz, 1H), 3.32 (dd, J=6.8 Hz and J=2.4 Hz, 1H), 3.22-3.21 (m, 3H); $^{31}$P NMR (162 MHz, $CD_3OD$) δ −23.6; ESI-HRMS m/z calculated for $C_{21}H_{32}NO_{18}P$ [M−H]$^-$: 616.1279; Found 616.1273.

Example 5

Biological Activity of Protected Compound

The compounds synthesised in Examples 1 to 4 were tested against the known target for T6P in vitro i.e. SnRK1, using the assay described in *Plant Physiol.* 2009, 149, 1860-1871. The assay was carried out in duplicate and it was quite clear that all four compounds were biologically inactive. These compounds did not inhibit SnRK1, as compared to T6P which shows typical inhibition (FIG. 1). This result clearly suggested that synthesised protected Examples 1 to 4 are themselves inactive.

Example 6

In vitro Deprotection

Two experimental techniques were chosen for studying the progress of deprotection experiments i.e. i) Mass spectroscopy and TLC (spot), and ii) P NMR. Progress of the reactions was monitored by looking for the disappearance of peak corresponding to protected compounds and appearance of peak corresponding to T6P. The structure of completely uncaged compound i.e. T6P was established by 1D and 2D NMR.

Both experimental techniques were very efficient and reproducible to analyse the deprotection experiments. Five millimolar solutions of Examples 1 to 4 were prepared in phosphate buffer (pH 7.4) and the resulting solution was exposed to different wavelengths of UV light and sunlight to monitor deprotection at different time intervals. The summary of deprotection experiments is given in Table 1.

TABLE 1

| Comp | Condition | | | | |
|---|---|---|---|---|---|
| | 125 W/ 365 nm | 125 W/ 200-400 nm | 8 W/ 365 nm | 8 W/ 254 nm | Sun light |
| NB-T6P, Ex 1 | 30 min | 15 min | 6 h | 4 h | 6 h |
| DMNB-T6P, Ex 2 | 60 min | 60 min | 10 h | 10 h | 8 h |
| NPE-T6P, Ex 3 | 20 min | 10 min | 90 min | 90 min | 90 min |
| Mono-DMNB-T6P, Ex 4 | 45 min | 45 min | 6 h | 10 h | 6 h |

Figure 2:
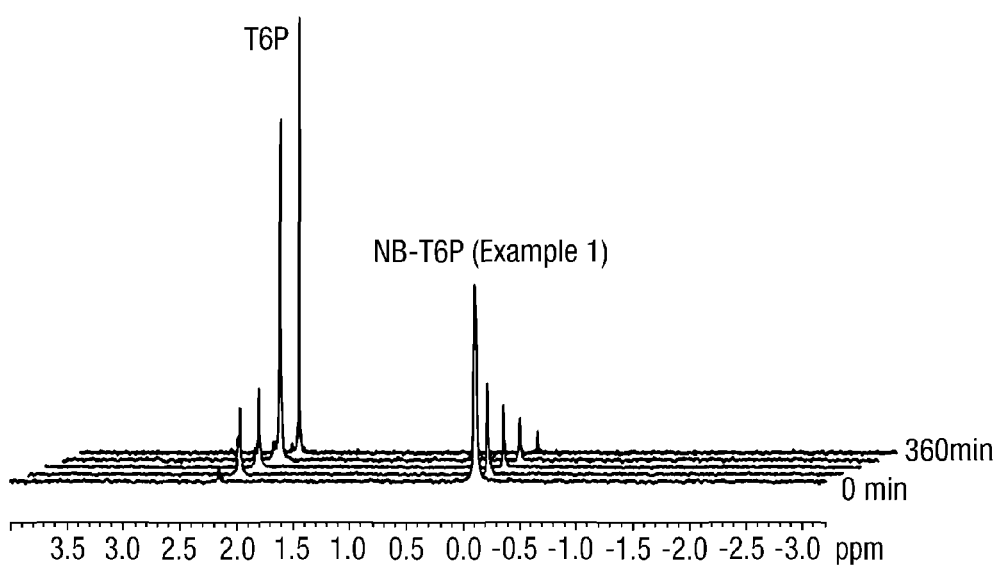
FIG. 2 shows the P NMR spectrum of Example 1 during the course of deprotection to remove the photolabile groups.

FIG. 2 shows the P NMR spectra which follow the uncaging of Example 1 (NB-T6P) (125 W/365 nm). This clearly shows the appearance of T6P peak and the disappearance of NB-T6P peak over the course of the deprotection reaction.

Figure 3:
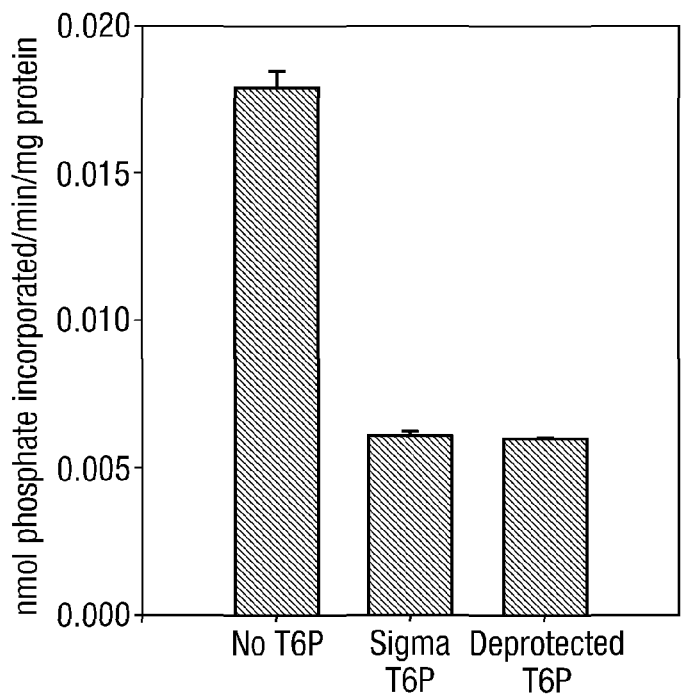
FIG. 3 shows the SnRK1 inhibition activity of trehalose-6-phosphate generated by deprotection of a compound of the invention, compared with commercial trehalose-6-phosphate.

T6P deprotected by treatment of NB-T6P (Example 1) under deprotection conditions of 125 W/365 nm radiation was included in SnRK1 assays (carried out in accordance with *Plant Physiol.* 2009, 149, 1860-1871) to determine its inhibition effect and compared to commercially available T6P from Sigma. The results are depicted in FIG. 3. As can be seen from the Figure, T6P obtained from deprotection of Example 1 inhibits SnRK1 in the same way as commercially available T6P at 0.32 mM concentration.

Example 7

Studies on in-planta Uptake

Aqueous solutions of each of Examples 1 to 4 were fed to roots of seedlings of *Arabidopsis thaliana* and after a certain period of time the aerial (shoot) part of seedling was harvested carefully and extracted in $H_2O$:MeOH (1:1) under liquid nitrogen to get crude fresh plant extract. The crude fresh plant extract thus obtained was analysed by mass spec and using HPLC to quantify the amount of compound taken up.

An aqueous solution of NB-T6P (Example 1) was fed to the seedlings, at 1 mM final concentration, near to the root and uptake was monitored in freshly prepared extract after 24 h, 48 h and 72 h using both HPLC and mass technique. It was found that there was average uptake 2.63 μg/10 mg of seedling in 24 h which increases to 6.05 μg/10 mg of seedling and 26.39 μg/10 mg of seedling respectively in 48 and 72 h. Increases in the amount of compounds in the plant over time clearly indicated that the uptake is irreversible.

Similarly Examples 2, 3 and 4 were also studied for uptake and it was found that all compounds were taken up by the plant in 72 h in different amounts dependent on the chemical structure of the molecule. DMNB-T6P (Example 2) was found in plant in 3.18 μg/10 mg of seedling concentration in 72 h where as mono-DMNB-T6P (Example 4) was noticed in concentration of 3.60 μg/10 mg of seedling in the same time.

The quantitative analysis of the compounds taken up into the plant was carried out using freshly prepared plant extract by LCMS and summarised data are given in Table 2.

The % uptake refers to the proportion of test compound fed to the plant which was taken up by the plant.

TABLE 2

Uptake of protected T6P compounds by *Arabidopsis* seedling after 72 h (3 days)

| Ex. No. | Compounds | uptake in μg/10 mg of seedling | SEM, n = 3 | Uptake % |
|---|---|---|---|---|
| 1 | NB-T6P, Ex. 1 | 26.39 | 6.81 | 14 |
| 2 | DMNB-T6P, Ex. 2 | 3.18 | 1.52 | 1 |
| 3 | NPE-T6P, Ex. 3 | 66.0 | 11.5 | 18 |
| 4 | Mono-DMNB-T6P, Ex. 4 | 3.60 | 0.82 | 1 |
| Comparative | T6P | — | — | — |

Example 8a

Synthesis of Caged Precursor of Glucose-6-phosphate [G6P(1-OMe)]

The compounds of the invention release nitroso aldehyde and ketone as a side product along with active molecule T6P after deprotection. Released side products are known to be biologically safe, but experiments were nevertheless undertaken to confirm whether the released side products cause any phenotypic change or enhance the biomass (starch) production in the plant. To this end, caged methyl glycosides of glucose-6-phosphate (G6P (1-OMe)) 14-16 were synthesised and included in further studies. The synthesis of these caged-G6P (1-OMe) was started from methyl 2,3,4-tri-O-(trimethylsilyl)-D-glucopyranoside 13 which was obtained from regioselective deprotection of trimethylsilyl group on persilylated methyl-D-glucopyranoside (Meldal et al, Carbohydr. Res. 235, 115-127 (1992)).

Thus, substrate 13 and bis(2-nitrobenzyl)-N,N-diisopropylphosphoramidite reagent 9 were reacted in the presence of 5.0 equiv of tetrazole (0.45 M soln in $CH_3CN$) in $CH_2Cl_2$ at 0° C.-RT overnight followed by oxidation with tBuOOH (0.1 mL) for 30 min and the resulting mixture was treated with Dowex-$H^+$ in methanol. The desired NB-caged G6P(1-OMe) 14 was produced in 50% isolated yield (Scheme 5). Similarly, phosphoramidite 10 and 11 were coupled with substrate 13 to provide DMNB-caged G6P(1-OMe) 15 and NPE-caged G6P (1-OMe) 16 in acceptable yield along with deprotected starting material.

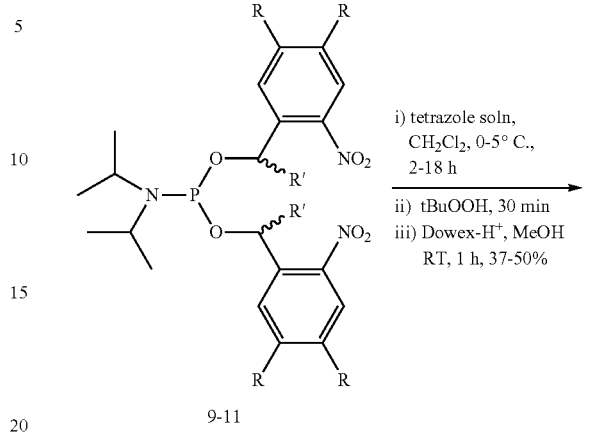

9-11 i) tetrazole soln, $CH_2Cl_2$, 0-5° C., 2-18 h
ii) tBuOOH, 30 min
iii) Dowex-$H^+$, MeOH RT, 1 h, 37-50%

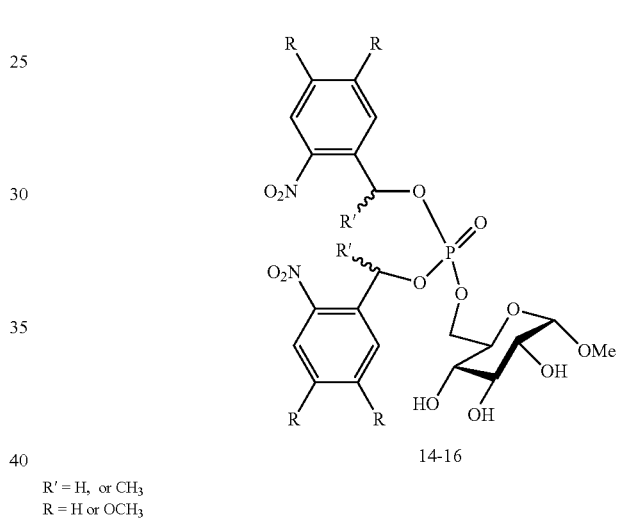

14-16

R' = H, or $CH_3$
R = H or $OCH_3$

When substrate 13 was treated with 1.0 equiv of $POCl_3$ in pyridine (Meldal et al, Carbohydr. Res. 235, 115-127 (1992)) for 10 min followed by the addition of 2.0 equiv of 4,5-dimethoxy-2-nitrobenzyl alcohol and stirring for 1 h, disubstituted- and monosubstituted-phosphates were obtained. The resulting mixture was stirred with Dowex-$H^+$ in methanol which gave DMNB-caged G6P(1-OMe) 15 and mono-DMNB-caged G6P(1-OMe) 17 in 18% and 49% isolable yields respectively (scheme 5a).

Scheme 5. Synthesis of caged G6P(1-OMe) 14-16.

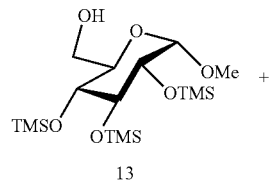

13

Scheme 5a. Synthesis of mono caged C6P(1-OMe) 17.

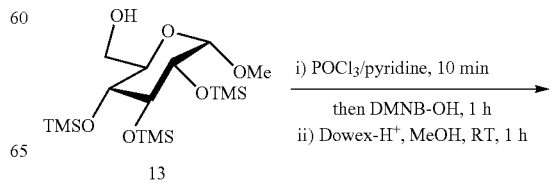

13 i) $POCl_3$/pyridine, 10 min
then DMNB-OH, 1 h
ii) Dowex-$H^+$, MeOH, RT, 1 h

-continued

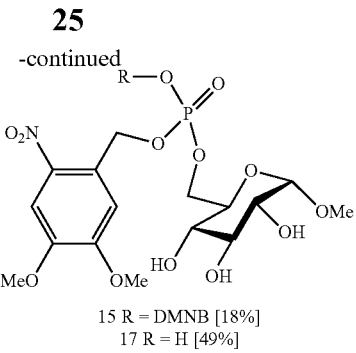

15 R = DMNB [18%]
17 R = H [49%]

Example 8b

Deprotection of Precursors of glucose-6-phosphate (Caged-G6P(1-OMe)) 14-17 in vitro After successful synthesis of protected-G6P(1-OMe) compounds their deprotection was carried out under various wavelength and power of UV light. The deprotection was also done under direct sunlight and data are summarised in Table 3.

TABLE 3

Deprotection of caged G6P(1-OMe) under various conditions

| Comp | Deprotection condition | | | | |
|---|---|---|---|---|---|
| | 125 W/ 365 nm | 125 W/ 200-400 nm | 8 W/ 365 nm | 8 W/ 254 nm | Sun light |
| NB-G6P(1-OMe) | 75 min | 45 min | 8 h | 6 h | 8 h |
| DMNB-G6P(1-OMe) | 120 min | 120 min | 10 h | 10 h | 10 h |
| NPE-G6P(1-OMe) | 75 min | 45 min | 2 h | 2 h | 10 h |
| Mono-DMNB-G6P(1-OMe) | 75 min | 75 min | 10 h | 10 h | 8 h |

Example 8c

Uptake of Protected Precursors of glucose-6-phosphate (Protected-G6P(1-OMe))

The protected-G6P(1-OMe) compounds were studied for in-planta uptake using the same method as Example 7 and it was found that compound 14 was taken up in trace amount after 72 h, whereas compounds 15, 16 and 17 were present in fairly in good concentration after the same period. The results are summarised in Table 4.

TABLE 4

Uptake of deprotected G6P(1-OMe) compounds by *Arabidopsis* seedling after 72 h (3 days)

| S. No. | Compounds | uptake in µg/10 mg of seedling | SEM, n = 3 | Uptake % |
|---|---|---|---|---|
| 1 | NB-G6P(1-OMe) | traces | — | trace |
| 2 | DMNB-G6P(1-OMe) | 2.22 | 1.52 | 1 |
| 3 | NPE-G6P(1-OMe) | 26.36 | 0.75 | 11 |
| 4 | Mono-DMNB-G6P(1-OMe) | 1.59 | 0.50 | 1 |
| 5 | G6P(1-OMe) | — | — | — |

Example 9

In-planta Release and Quantification of T6P Using 2DG6P as Internal Standard

Examples 1 to 4 were fed to three week old *Arabidopsis thaliana* plants and after 72 h the seedling was irradiated using different power and length of UV light, including sunlight. The seedlings were harvested and plant extract prepared. The fresh plant extract was processed in accordance with the methods described by Delatte et al (*Anal. Biochem.* 2009, 389, 12-17), and the released T6P quantified using LCMS.

Plants growing in agar medium in Phytatrays were treated with one of Examples 1 to 4 by adding 10 µl of 50 mM solution of the chosen compound in water to the agar medium, resulting in 1.0 mM final concentration in the agar medium for Examples 1, 2 and 4. In the case of NPE-T6P (Example 3), the final concentration was 0.1 mM. Contact with aerial parts of the plants was avoided. The plants were grown for a further three days (uptake, 72 h) and hardened off to prevent wilting by partially opening the Phytatrays. On the third day plants were exposed to UV or sunlight treatment. UV treatments consisted of 8 hr exposure to natural daylight, 8 hr exposure to a 100 W UV spotlight at a distance of 18 cm or two 8 hr periods of exposure to an 8 W UV bulb at a distance of 6 cm over two days. Control plants (fed with compounds) were treated under the same conditions but without UV light (except for daylight treatment). After exposure to light, the aerial parts of the plants were quickly harvested, weighed and frozen in liquid nitrogen.

Harvested plant material was extracted by liquid/liquid extraction (LLE) followed by solid phase extraction (SPE) according to Delatte et al (Anal. Biochem. 389, 12-17 (2009)). For LLE/SPE extractions around 25 mg plant tissue were used pooled from several plants. Samples were dissolved in 50 µl of $H_2O$:MeOH (1:1) and subjected for T6P analysis using 10 µl injection under LC-MS (Quattro) condition.

The quantification of in planta released T6P was carried out by using a calibration curve which was recorded using 2DG6P (30 µM) as internal standard with different known concentration of T6P as per the method described by Yang et al (*ChemBioChem* 2005, 6, 346-357). From the single ion recording (SIR) data obtained by LC-MS (Quattro), extracted ion chromatograms using 2DG6P as internal standard corresponding to T6P and 2DG6P were generated (421 and 243 m/z). These are depicted in FIG. 5. FIG. 5(*a*) provides chromatograms showing the natural presence of T6P in trace amount along with S6P (sucrose-6-phosphate). FIG. 5(*b*) provides chromatograms showing the higher concentration of in-planta released T6P along with internal standard 2DG6P.

Figure 4:
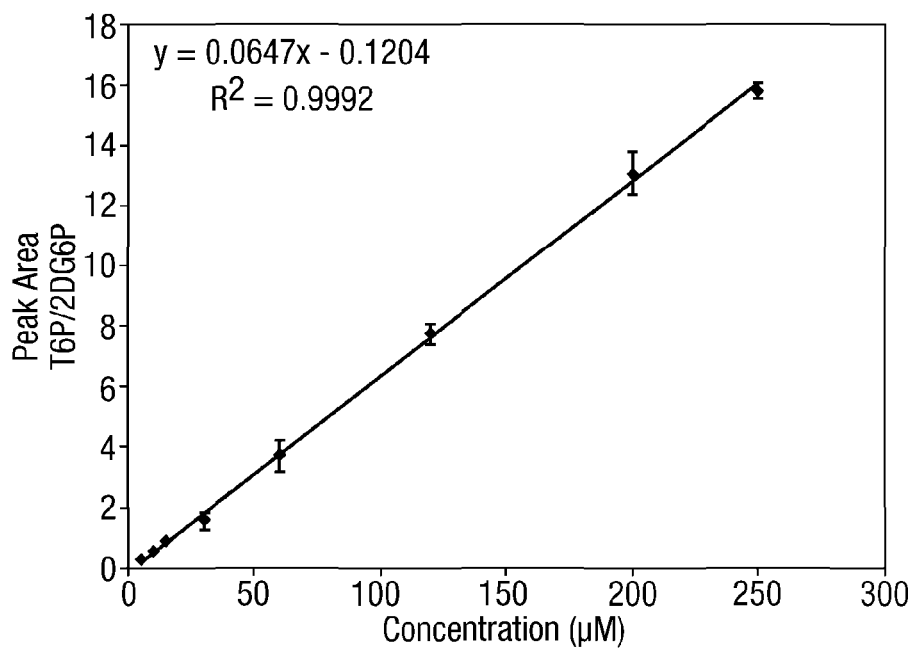
FIG. 4 provides a calibration curve for trehalose-6-phosphate using 2DG6P as an internal standard.

Peak area from these extracted ion chromatograms were integrated to determine the T6P/2DG6P ratio. A calibration curve of peak ratio (T6P/2DG6P) vs concentration (µM) was generated. Seven points were used to generate the calibration curve using a T6P concentration in the range of 5 µM to 250 µM and a constant concentration 30 µM of 2DG6P. From sample analyses, T6P/2DG6P peak areas were determined and the T6P concentration was then inferred from the calibration curve (FIG. 4).

The amount of released T6P in-planta depends on the nature of the compound used, the source of light and power of light. Similar was found during in-vitro experiments.

The calculated amount of T6P in planta are summarised in Table 5. From the table it was quite clear that there was sufficient amount of T6P released in planta depending on light source. The maximum amount of T6P was released when the chemical-fed plants were irradiated with 100 W light in all cases. Notably, under sunlight irradiation all of Examples 1 to 4 released in-planta T6P in sufficient amount ranging from 61.0 to 153 µM. In-planta release of T6P under sunlight further supports the direct application of these compounds in the improvement of crop yield and the increase in starch production in plants. The higher concentration T6P was also noticed in the plants which were fed with compounds of the invention and grown in growth light indicating that in-planta release of T6P is very efficient. Most importantly the amount of in-planta T6P can be controlled by selecting the light sources and time of irradiation or selecting the appropriate compound. These data indicated the release of T6P in-planta was very broad spectrum which is advantageous in providing control over the effects on the plants treated.

TABLE 5

Amount of in-planta released T6P under various condition in µM and µg/10 mg of seedling

| Ex. No. | Compounds | | 100 W UV 8 h | 8 W UV 16 h | Sun light 8 h | Growth light 8 h | Growth light 16 h |
|---|---|---|---|---|---|---|---|
| 1 | NB-T6P | Conc. T6P (µM) | 223.81 | 97.69 | 58.28 | 4.95 | 26.44 |
| | | T6P (µg/10 mg of seedling) | 2.36 | 0.82 | 0.54 | 0.05 | 0.24 |
| 2 | DMNB-T6P | Conc. T6P (µM) | 230.97 | 61.58 | 71.78 | 11.96 | 17.22 |
| | | T6P (µg/10 mg of seedling) | 3.75 | 0.57 | 0.60 | 0.10 | 0.14 |
| 3‡ | NPE-T6P | Conc. T6P (µM) | 22.11 | 17.20 | 19.97 | 12.62 | 9.93 |
| | | T6P (µg/10 mg of seedling) | 0.23 | 0.13 | 0.17 | 0.09 | 0.07 |
| 4 | Mono-DMNB-T6P | Conc. T6P (µM) | 234.16 | 75.12 | 148.07 | 30.45 | 83.31 |
| | | T6P (µg/10 mg of seedling) | 3.09 | 0.64 | 1.25 | 0.23 | 1.84 |
| Comparative | T6P† | Conc. T6P (µM) | 4.80 | 4.80 | 4.80 | 4.80 | 4.80 |
| | | T6P (µg/10 mg of seedling) | 0.13 | 0.13 | 0.13 | 0.13 | 0.13 |
| Comparative | H₂O | Conc. T6P (µM) | 3.72 | 4.18 | 4.49 | 3.72 | 3.72 |
| | | T6P (µg/10 mg of seedling) | 0.03 | 0.04 | 0.04 | 0.03 | 0.03 |

†These plants were not irradiated with light.
‡NPE-caged compound was fed in 0.1 mM final concentration as compared to others which were given in 1.0 mM final concentration.

Example 10

Increased Starch Production

Figure 6:
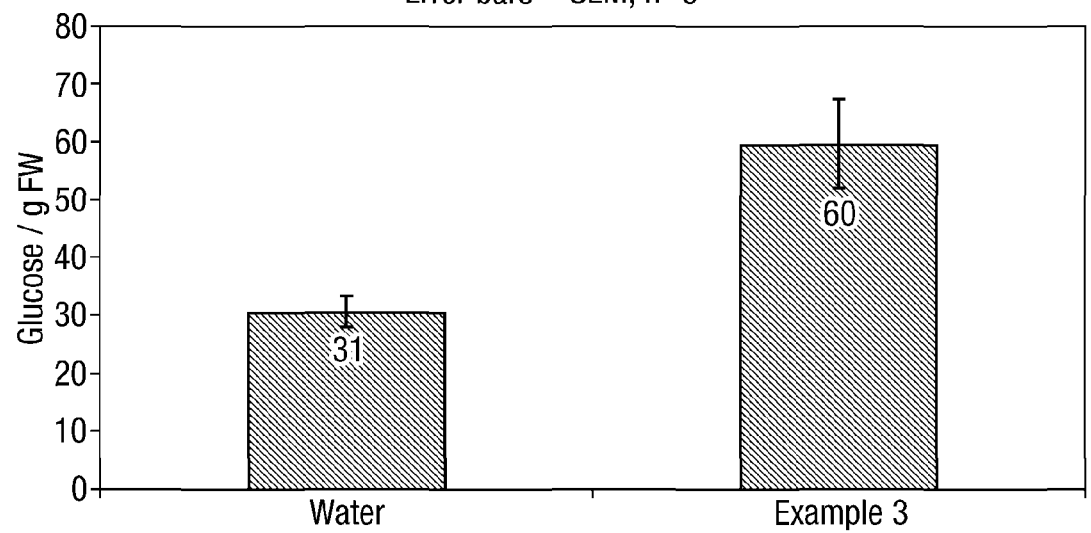
FIG. 6 shows the effect of a compound of the invention on the starch levels in a plant.

Pre-stratified *Arabidopsis thaliana* seeds were sown in sterile culture on 0.5 mL solid medium (0.5× Murashige and Skoog with Gamborg's vitamins, 0.5% agar) in 0.5 mL tubes pierced with a small hole in the bottom. Tubes were arrayed in polystyrene racks and floated in liquid medium without added sucrose in Phytatrays. Seedlings were grown under 12 hr days under fluorescent lights giving 250 µmo/m²/s, and 23° C. day/18° C. night temperatures. At 16-20 days after sowing the liquid medium was removed and the tubes were sealed with electrician's tape. All plants were topped up with 0.5×MS medium with no sucrose. Plants were treated with compound example 3, or water by adding example 3 to a final concentration of 0.1 mM in the media. On the third day plants were subjected to growth lights supplemented with UV light (8 W UV bulb) from a Gelman transilluminator (Model 51438) at a distance of 6 cm for 8 h. Plants were allowed to recover for a further day and the aerial parts were harvested at the end of the day, weighed and frozen in liquid nitrogen. Starch was extracted according to published methods, converted to glucose and measured as nmol glucose/gram fresh weight (*Nature Protocol* 2006, 1, 1342). Results are depicted in FIG. 6. Plants treated with example 3 show significantly higher starch levels compared to plants treated with water only. The increase in amount of starch produced was tenfold higher than the concentration of T6P released in-planta from example 3 used to produce this starch increase. This experiment shows a direct biological alteration of plant metabolism by the controlled release of T6P.

The invention claimed is:
1. A compound which is a trehalose-6-phosphate or trehalose-6-phosphonate precursor of formula (I) or an agriculturally acceptable salt thereof:

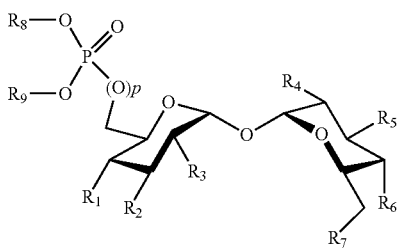

(I)

wherein:

p is 0 or 1;

$R_1$ to $R_7$ independently represent F, $N_3$, NR'R", $C_{1-4}$alkyl, —($C_{1-4}$alkyl)OH or OH, wherein R' and R" independently represent hydrogen or $C_{1-4}$alkyl; and $R_8$ and $R_9$ are the same or different and represent H or a photolabile protecting group, wherein at least one of $R_8$ and $R_9$ represents a photolabile protecting group.

2. A composition comprising a compound as defined in claim 1 together with an agriculturally acceptable carrier or diluent.

3. A method of increasing starch production in a plant, which method comprises treating the plant or the locus of the plant with an effective amount of a compound according to claim 1 or a composition according to claim 2.

4. A method of increasing crop yield, which method comprises treating the crop or a locus of the crop with an effective amount of a compound according to claim 1 or a composition according to claim 2.

5. A method of reducing the incidence of pre-harvest sprouting of a crop, which method comprises treating the crop or the locus of the crop with an effective amount of a compound according to claim 1 or a composition according to claim 2.

6. The compound according to claim 1, wherein the photolabile protecting group is of formula (II):

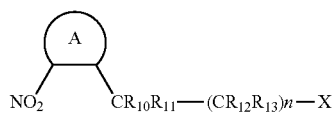

(II)

wherein ring A represents an aryl or heterocyclic group;

either (i) $R_{10}$ and $R_{11}$ are the same or different and are selected from hydrogen, $C_{1-4}$ alkyl which is unsubstituted or substituted with one or more halogen atoms, —OR', halogen, —NR'R" or —CO$_2$R', wherein R' and R" are independently selected from hydrogen and $C_{1-4}$ alkyl, or (ii) two $R_{10}$ groups on adjacent photolabile protecting groups together form a bond and $R_{11}$ represents hydrogen, $C_{1-4}$ alkyl which is unsubstituted or substituted with one or more halogen atoms, —OR', halogen, —NR'R" or —CO$_2$R', wherein R' and R" are independently selected from hydrogen and $C_{1-4}$ alkyl;

n is 0 or 1; and $R_{12}$ and $R_{13}$ are the same or different and are selected from hydrogen, $C_{1-4}$ alkyl which is unsubstituted or substituted with one or more halogen atoms, —OR', halogen, —NR'R" or —CO$_2$R', wherein R' and R" are independently selected from hydrogen and $C_{1-4}$ alkyl;

wherein X represents a link to the remainder of the compound of formula (I).

7. The compound according to claim 6, wherein ring A represents a $C_{6-10}$ aryl group or a 5- to 14-membered heterocyclic group containing one or more atoms selected from N, O and S, wherein the aryl or heterocyclic group is unsubstituted or substituted with one or more substituents selected from $C_{1-4}$ alkyl, —OR', halogen, CN, —NR'R",
—COOR', —($C_{1-4}$alkyl)COOR' and —O($C_{1-4}$alkyl) COOR', wherein R' and R" are independently selected from hydrogen and $C_{1-4}$ alkyl, or wherein two adjacent substituents on the aryl or heterocyclic group together form a 5- or 6-membered heterocyclic ring containing one or more heteroatoms selected from N, O or S.

8. The compound according to claim 7, wherein ring A represents a phenyl, naphthalenyl or dibenzofuranyl ring.

9. The compound according to claim 1, wherein the photolabile protecting group is of formula (IIa):

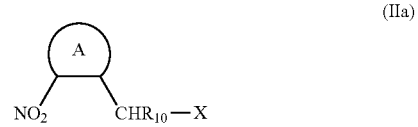

(IIa)

wherein ring A represents an unsubstituted or substituted group selected from phenyl, naphthyl or dibenzofuranyl, wherein a substituted phenyl, naphthyl or dibenzofuranyl group is a phenyl, naphthyl or dibenzofuranyl group having one or two methoxy substituents, or a phenyl, naphthyl or dibenzofuranyl group wherein two adjacent ring positions are substituted with a —CH$_2$—O—CH$_2$—moiety; and $R_{10}$ represents hydrogen, methyl, —CF$_3$ or —COOH;

wherein X represents a link to the remainder of the compound of formula (I).

10. The compound according to claim 1, wherein the photolabile group is selected from

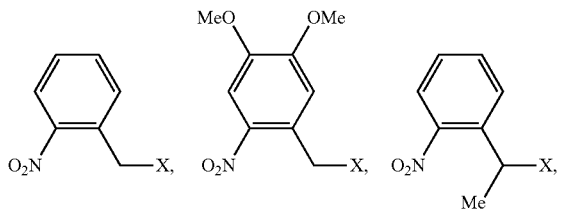

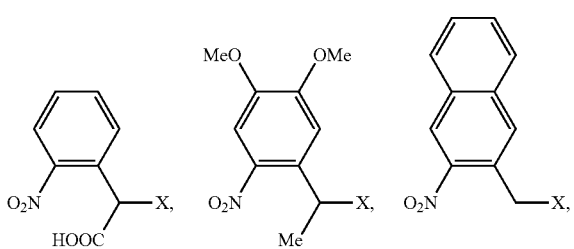

-continued

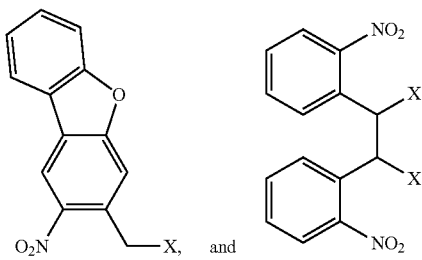

and

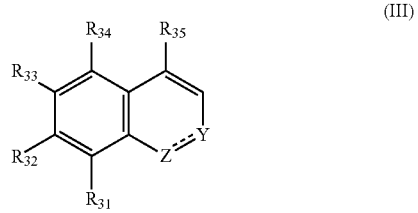

wherein X represents a link to the remainder of the compound of formula (I).

11. The compound according to claim 1, wherein the photolabile protecting group is of formula (III):

(III)

wherein either Z represents N, Y represents $CR_{36}$ and Z and Y are linked by a double bond; or Z represents O, Y represents C=O and Z and Y are linked by a single bond;

$R_{36}$ represents —$CR_{37}R_{38}X$;

when Y represents $CR_{36}$, $R_{35}$ represents hydrogen, and when Y represents C=O, $R_{35}$ represents —$CR_{37}R_{38}X$;

either (i) $R_{37}$ and $R_{38}$ are the same or different and are selected from hydrogen, $C_{1-4}$ alkyl which is unsubstituted or substituted with one or more halogen atoms, —OR', halogen, —NR'R" or —$CO_2R'$, wherein R' and R" are independently selected from hydrogen and $C_{1-4}$ alkyl, or (ii) two $R_{37}$ groups on adjacent photolabile protecting groups together form a bond and $R_{38}$ represents hydrogen, $C_{1-4}$ alkyl which is unsubstituted or substituted with one or more halogen atoms, —OR', halogen, —NR'R" or —$CO_2R'$ wherein R' and R" are independently selected from hydrogen and $C_{1-4}$ alkyl;

$R_{32}$ represents —OR', —NR'R", —O($C_{1-4}$alkyl)-COOR', —O($C_{1-4}$alkyl)-OR' or —O($C_{1-4}$alkyl)-NR'R", wherein R' and R" independently represent hydrogen or $C_{1-4}$ alkyl; and $R_{31}$, $R_{33}$ and $R_{34}$ are independently selected from hydrogen, halogen, —OR', —NR'R", —O($C_{1-4}$alkyl)-COOR', —O($C_{1-4}$alkyl)-OR' or —O($C_{1-4}$alkyl)-NR'R", wherein R' and R" independently represent hydrogen or $C_{1-4}$ alkyl;

wherein X represents a link to the remainder of the compound of formula (I).

12. The compound according to claim 11, wherein the photolabile protecting group is of formula (IIIa)

(IIIa)

wherein $R_{32}$ represents —OR', —NR'R" or —O($C_{1-4}$alkyl)-COOR', wherein R' and R" independently represent hydrogen or $C_{1-2}$ alkyl; and $R_{33}$ represents hydrogen, Br, —OR', —NR'R" or —O($C_{1-4}$alkyl)-COOR', wherein R' and R" independently represent hydrogen or $C_{1-2}$ alkyl;

wherein X represents the link to the remainder of the compound of formula (I).

13. The compound according to claim 12, wherein a) $R_{33}$ represents H and $R_{32}$ represents OMe, $NMe_2$, $NEt_2$ or —$OCH_2COOH$; or b) $R_{33}$ represents Br and $R_{32}$ represents OH; or c) $R_{33}$ and $R_{32}$ both represent —$OCH_2COOH$.

14. The compound according to claim 1, wherein the photolabile protecting group is selected from

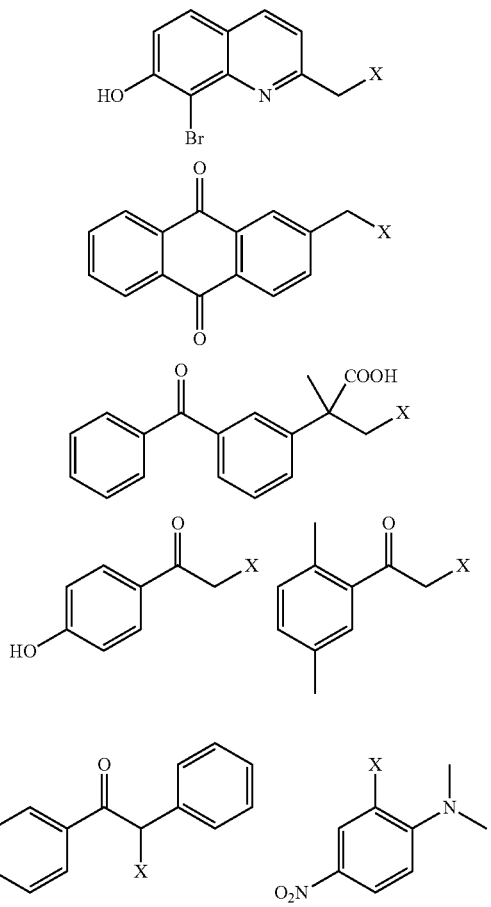

-continued
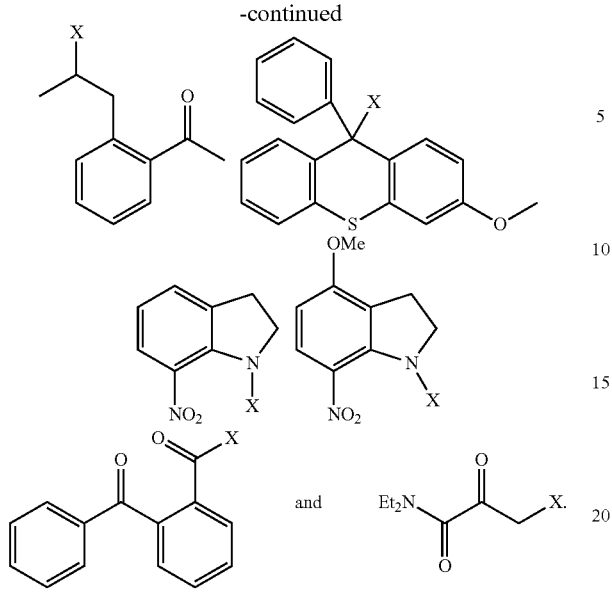
15. The compound according to claim 1, wherein $R_1$ to $R_7$ represent OH.
16. The compound according to claim 1, wherein p is 1.
* * * * *